US011510805B2

(12) United States Patent
Kaiser et al.

(10) Patent No.: US 11,510,805 B2
(45) Date of Patent: Nov. 29, 2022

(54) ANATOMICAL GRIPPING SYSTEM FOR GRIPPING THE LEG AND FOOT OF A PATIENT WHEN EFFECTING HIP DISTRACTION AND/OR WHEN EFFECTING LEG POSITIONING

(71) Applicant: Stryker Corp., Kalamazoo, MI (US)

(72) Inventors: William Kaiser, Campbell, CA (US); Ian Kovacevich, Carlsbad, CA (US); Jeremy Graul, Elk Grove, CA (US); John Parker, Sunnyvale, CA (US); Nouphone Bansasine, San Diego, CA (US); James Flom, Redwood City, CA (US)

(73) Assignee: Stryker Corp., Kalamazoo, MI (US)

( * ) Notice: Subject to any disclaimer, the term of this patent is extended or adjusted under 35 U.S.C. 154(b) by 615 days.

(21) Appl. No.: 15/889,998

(22) Filed: Feb. 6, 2018

(65) Prior Publication Data
US 2018/0221190 A1    Aug. 9, 2018

Related U.S. Application Data

(60) Provisional application No. 62/455,154, filed on Feb. 6, 2017, provisional application No. 62/546,629, filed on Aug. 17, 2017.

(51) Int. Cl.
*A61F 5/37* (2006.01)
*A61B 17/02* (2006.01)
(Continued)

(52) U.S. Cl.
CPC .............. *A61F 5/37* (2013.01); *A61B 17/025* (2013.01); *A61G 13/1245* (2013.01);
(Continued)

(58) Field of Classification Search
CPC ........ A61F 5/37; A61F 5/3761; A61F 5/0111; A61F 5/0127; A61F 5/0195;
(Continued)

(56) References Cited

U.S. PATENT DOCUMENTS

| 2,150,314 A | 3/1939 | Bell |
| D130,079 S | 10/1941 | Weller |

(Continued)

FOREIGN PATENT DOCUMENTS

| DE | 10 2005 023 477 | 11/2006 |
| DE | 20 2009 003 314 | 7/2009 |

(Continued)

OTHER PUBLICATIONS

Hip Distraction System: Advanced solutions for supine hip arthroscopy procedures, Arthrex, 2013, pp. 1-6.
(Continued)

*Primary Examiner* — Erin Deery
*Assistant Examiner* — Daniel A Miller
(74) *Attorney, Agent, or Firm* — Pandiscio & Pandiscio, P.C.

(57) ABSTRACT

An anatomical gripping system comprising: a binding comprising: a substantially rigid spine; a calf shell mounted to the substantially rigid spine; an anterior shell; and a clamping mechanism connecting the anterior shell to the calf shell; wherein the calf shell comprises a flexible portion configured to selectively engage the superior portion of the calcaneus bone of a patient; and further wherein when the clamping mechanism applies a force to the flexible portion of the calf shell, the flexible portion of the calf shell is drawn into engagement with the superior portion of the calcaneus bone of the patient.

33 Claims, 38 Drawing Sheets

(51) Int. Cl.
*A61G 13/12* (2006.01)
*A61B 17/00* (2006.01)
*A61B 17/88* (2006.01)
*A61B 17/66* (2006.01)
*A61G 13/00* (2006.01)

(52) U.S. Cl.
CPC .......... *A61B 17/66* (2013.01); *A61B 17/8866* (2013.01); *A61B 2017/00477* (2013.01); *A61G 13/0081* (2016.11); *A61G 13/125* (2013.01)

(58) Field of Classification Search
CPC ..... A61F 5/0585; A61B 17/025; A61B 17/66; A61B 17/8866; A61G 13/1245; A61G 13/0009; A61G 13/125; A61G 13/0081; A61G 7/075; A61G 7/0755; A61G 15/005; A61G 15/12; A63C 9/00; A63C 9/005; A63C 9/245; A63C 10/00; A63C 10/01; A63C 10/14; A63C 10/145; A63C 10/106; A63C 13/001; A63C 1/00; A63C 1/02; A63C 1/04; A63C 1/222; A43B 5/00; A43B 5/16; A43B 5/1616; A43B 5/04; A43B 5/0401; A43B 5/0403; A43B 5/0411; A43B 5/0417; A43B 5/0421; A43B 5/0405; A47C 20/21
USPC ................................................ 128/869, 882
See application file for complete search history.

(56) References Cited

U.S. PATENT DOCUMENTS

| | | |
|---|---|---|
| D171,677 S | 3/1954 | Adler |
| 3,220,022 A | 11/1965 | Nelson |
| D221,035 S | 6/1971 | Raines et al. |
| 3,745,996 A | 7/1973 | Rush, Sr. |
| 3,808,644 A | 5/1974 | Schoch |
| D264,531 S | 5/1982 | Trode |
| 4,539,763 A | 9/1985 | Walkhoff |
| 4,551,932 A | 11/1985 | Schoch |
| 4,573,482 A | 3/1986 | Williams, Jr. |
| 4,708,510 A | 11/1987 | McConnell et al. |
| 4,835,886 A | 6/1989 | Chemello et al. |
| 4,841,650 A | 6/1989 | Dodge et al. |
| 4,865,303 A | 9/1989 | Hall |
| 5,052,128 A * | 10/1991 | Lonardo ............ A61G 5/10 36/11.5 |
| 5,162,039 A | 11/1992 | Dahners |
| 5,177,882 A | 1/1993 | Berger |
| 5,249,377 A | 10/1993 | Walkhoff |
| 5,287,575 A | 2/1994 | Allen et al. |
| 5,306,231 A | 4/1994 | Cullum et al. |
| 5,560,577 A | 10/1996 | Keselman |
| 5,582,379 A | 12/1996 | Keselman et al. |
| 5,608,934 A | 3/1997 | Torrie et al. |
| D385,040 S | 10/1997 | Keselman |
| D387,581 S | 12/1997 | Parker et al. |
| 5,702,389 A | 12/1997 | Taylor et al. |
| D389,580 S | 1/1998 | Keselman et al. |
| 5,728,095 A | 3/1998 | Taylor et al. |
| 5,819,440 A | 10/1998 | Okajima |
| 5,918,330 A | 7/1999 | Navarro et al. |
| 5,971,984 A | 10/1999 | Taylor et al. |
| 6,109,625 A | 8/2000 | Hewitt |
| 6,162,223 A | 12/2000 | Orsak et al. |
| 6,286,164 B1 | 9/2001 | Lamb et al. |
| 6,678,908 B2 | 1/2004 | Borders et al. |
| D546,599 S | 7/2007 | Goldberg |
| 7,237,556 B2 | 7/2007 | Smothers et al. |
| 7,337,483 B2 | 3/2008 | Boucher et al. |
| 7,343,635 B2 | 3/2008 | Jackson |
| 7,477,926 B2 | 1/2009 | McCombs |
| 7,520,007 B2 | 4/2009 | Skripps |
| 7,520,008 B2 | 4/2009 | Wong et al. |
| 7,565,708 B2 | 7/2009 | Jackson |
| 7,572,292 B2 | 8/2009 | Crabtree et al. |
| 7,591,050 B2 | 9/2009 | Hammerslag |
| 7,600,281 B2 | 10/2009 | Skripps |
| 7,669,262 B2 | 3/2010 | Skripps et al. |
| 7,677,249 B2 | 3/2010 | Kong et al. |
| 7,739,762 B2 | 6/2010 | Lamb et al. |
| RE41,412 E | 7/2010 | Van Steenburg |
| 7,762,975 B2 | 7/2010 | Memminger |
| 7,832,401 B2 | 11/2010 | Torrie et al. |
| 7,862,570 B2 | 1/2011 | Russell et al. |
| 7,878,992 B2 | 2/2011 | Mitsuishi et al. |
| 7,882,583 B2 | 2/2011 | Skripps |
| 7,947,006 B2 | 5/2011 | Torrie et al. |
| 7,949,006 B2 | 5/2011 | Jagadesan et al. |
| 7,949,386 B2 | 5/2011 | Buly et al. |
| 7,979,932 B2 | 7/2011 | Liang |
| 8,011,045 B2 | 9/2011 | Skripps |
| 8,037,884 B2 | 10/2011 | Weinstein et al. |
| 8,055,487 B2 | 11/2011 | James |
| 8,060,960 B2 | 11/2011 | Jackson |
| 8,109,942 B2 | 2/2012 | Carson |
| 8,152,816 B2 | 4/2012 | Tuma et al. |
| D665,912 S | 8/2012 | Skripps |
| 8,234,730 B2 | 8/2012 | Skripps |
| 8,234,731 B2 | 8/2012 | Skripps |
| 8,256,050 B2 | 9/2012 | Wong et al. |
| 8,281,434 B2 | 10/2012 | Skripps |
| 8,322,342 B2 | 12/2012 | Soto et al. |
| 8,388,553 B2 | 3/2013 | James et al. |
| 8,397,323 B2 | 3/2013 | Skripps et al. |
| 8,413,660 B2 | 4/2013 | Weinstein et al. |
| 8,464,720 B1 | 6/2013 | Pigazzi et al. |
| 8,469,911 B2 | 6/2013 | Hiebert |
| 8,486,070 B2 | 7/2013 | Morgan et al. |
| 8,491,597 B2 | 7/2013 | Russell et al. |
| 8,491,664 B2 | 7/2013 | McMahon et al. |
| 8,511,314 B2 | 8/2013 | Pigazzi et al. |
| 8,545,570 B2 | 10/2013 | Crabtree et al. |
| 8,555,439 B2 | 10/2013 | Soto et al. |
| 8,570,187 B2 | 10/2013 | Janna et al. |
| 8,611,697 B2 | 12/2013 | Nathaniel et al. |
| 8,679,187 B2 | 3/2014 | Allen et al. |
| 8,690,806 B2 | 4/2014 | Hiebert |
| 8,690,807 B2 | 4/2014 | Hiebert |
| 8,702,712 B2 | 4/2014 | Jordan et al. |
| 8,707,484 B2 | 4/2014 | Jackson et al. |
| 8,707,486 B2 | 4/2014 | Chella et al. |
| 8,719,979 B2 | 5/2014 | Jackson |
| 8,721,643 B2 | 5/2014 | Morgan et al. |
| 8,795,312 B2 | 8/2014 | Fan et al. |
| 8,806,679 B2 | 8/2014 | Soto et al. |
| 8,826,474 B2 | 9/2014 | Jackson |
| 8,826,475 B2 | 9/2014 | Jackson |
| 8,828,009 B2 | 9/2014 | Allen et al. |
| 8,833,707 B2 | 9/2014 | Steinberg et al. |
| 8,839,471 B2 | 9/2014 | Jackson |
| 8,844,077 B2 | 9/2014 | Jackson et al. |
| 8,845,568 B2 | 9/2014 | Clark et al. |
| 8,856,986 B2 | 10/2014 | Jackson |
| 8,890,511 B2 | 11/2014 | Belew |
| 8,893,333 B2 | 11/2014 | Soto et al. |
| 8,894,716 B2 | 11/2014 | McMahon et al. |
| 8,938,826 B2 | 1/2015 | Jackson |
| 8,944,065 B2 | 2/2015 | Slusarz, Jr. |
| 8,945,026 B2 | 2/2015 | Moser et al. |
| 8,978,180 B2 | 3/2015 | Jackson |
| 8,986,228 B2 | 3/2015 | Auchinleck et al. |
| 8,997,284 B2 | 4/2015 | Kreuzer et al. |
| 8,997,286 B2 | 4/2015 | Wyslucha et al. |
| 8,997,749 B2 | 4/2015 | Drake et al. |
| 9,056,012 B2 | 6/2015 | Crabtree, Jr. et al. |
| 9,072,646 B2 | 7/2015 | Skripps et al. |
| 9,085,915 B1 | 7/2015 | Emmett |
| 9,101,393 B2 | 8/2015 | Jordan et al. |
| 9,107,792 B2 | 8/2015 | Catacchio et al. |
| 9,119,610 B2 | 9/2015 | Matta et al. |
| 9,161,875 B2 | 10/2015 | Clark et al. |
| 9,161,876 B2 | 10/2015 | Pigazzi et al. |

(56) References Cited

U.S. PATENT DOCUMENTS

| | | |
|---|---|---|
| 9,173,649 B2 | 11/2015 | Clark et al. |
| 9,180,062 B2 | 11/2015 | Jackson |
| 9,186,291 B2 | 11/2015 | Jackson et al. |
| 9,198,817 B2 | 12/2015 | Jackson |
| 9,205,013 B2 | 12/2015 | Jackson |
| 9,211,223 B2 | 12/2015 | Jackson |
| 9,226,865 B2 | 1/2016 | Jackson |
| 9,233,043 B2 | 1/2016 | Labedz et al. |
| 9,265,679 B2 | 2/2016 | Jackson |
| 9,289,342 B2 | 3/2016 | Jackson |
| 9,295,433 B2 | 3/2016 | Jackson et al. |
| 9,295,556 B2 | 3/2016 | Perez, III et al. |
| 9,301,897 B2 | 4/2016 | Jackson |
| 9,308,145 B2 | 4/2016 | Jackson |
| 9,364,380 B2 | 6/2016 | Jackson |
| 9,456,945 B2 | 10/2016 | Jackson |
| 9,468,576 B2 | 10/2016 | Jackson |
| 9,510,987 B2 | 12/2016 | Jackson et al. |
| 9,549,865 B2 | 1/2017 | Hiebert |
| 9,610,206 B2 | 4/2017 | Jackson |
| 9,672,662 B2 | 6/2017 | Scanlan et al. |
| 9,750,656 B1 | 9/2017 | Pigazzi et al. |
| 9,782,287 B2 | 10/2017 | Pigazzi et al. |
| 9,931,262 B2 | 4/2018 | Pigazzi et al. |
| 9,936,941 B2 | 4/2018 | Weisel et al. |
| 9,949,883 B1 | 4/2018 | Pigazzi et al. |
| 10,034,806 B1 | 7/2018 | Greenhalgh, Sr. |
| D832,334 S | 10/2018 | Kushner et al. |
| 10,130,542 B1 | 11/2018 | Strawder |
| 10,159,520 B2 | 12/2018 | Krickeberg et al. |
| 2002/0023298 A1 | 2/2002 | Lamb et al. |
| 2004/0003468 A1 | 1/2004 | Mitsuishi et al. |
| 2004/0092854 A1 | 5/2004 | D'Amico |
| 2004/0133979 A1 | 7/2004 | Newkirk et al. |
| 2004/0133983 A1 | 7/2004 | Newkirk et al. |
| 2005/0160533 A1 | 7/2005 | Boucher et al. |
| 2006/0047228 A1 | 3/2006 | Petelenz et al. |
| 2006/0074366 A1 | 4/2006 | Ryan et al. |
| 2006/0100562 A1 | 5/2006 | Pamplin |
| 2006/0130713 A1 | 6/2006 | Jones et al. |
| 2006/0185090 A1 | 8/2006 | Jackson |
| 2006/0271056 A1 | 11/2006 | Terrill-Grisoni et al. |
| 2007/0161935 A1* | 7/2007 | Torrie ............... A61G 13/0036 602/32 |
| 2007/0251011 A1 | 11/2007 | Matta et al. |
| 2007/0277350 A1 | 12/2007 | Hines |
| 2008/0214976 A1 | 9/2008 | Memminger et al. |
| 2008/0216231 A1 | 9/2008 | Lambarth et al. |
| 2008/0309052 A1* | 12/2008 | Neiley ............... A63C 10/18 280/613 |
| 2009/0287128 A1* | 11/2009 | Ingimundarson ..... A61F 5/0102 602/27 |
| 2011/0009791 A1* | 1/2011 | Hopmann ............. A61F 5/0585 602/23 |
| 2011/0023893 A1 | 2/2011 | Striggow et al. |
| 2011/0119829 A1 | 5/2011 | Skripps et al. |
| 2011/0190676 A1 | 8/2011 | Torrie et al. |
| 2012/0059376 A1 | 3/2012 | Rains et al. |
| 2012/0073476 A1 | 3/2012 | Lai |
| 2012/0204885 A1 | 8/2012 | Koch |
| 2012/0233782 A1 | 9/2012 | Kreuzer et al. |
| 2012/0240938 A1 | 9/2012 | Pamichev |
| 2012/0255122 A1 | 10/2012 | Diel et al. |
| 2012/0259261 A1 | 10/2012 | Clark et al. |
| 2012/0259343 A1 | 10/2012 | Clark et al. |
| 2012/0305005 A1 | 12/2012 | Keith-Lucas et al. |
| 2012/0305006 A1* | 12/2012 | Keith-Lucas ........ A61G 13/125 128/845 |
| 2013/0081635 A1 | 4/2013 | Drake et al. |
| 2013/0111666 A1 | 5/2013 | Jackson |
| 2013/0133137 A1 | 5/2013 | Jackson et al. |
| 2013/0174853 A1 | 7/2013 | Pigazzi |
| 2013/0191994 A1 | 8/2013 | Bellows et al. |
| 2013/0199541 A1 | 8/2013 | Sluss et al. |
| 2013/0269710 A1 | 10/2013 | Hight et al. |
| 2013/0312187 A1 | 11/2013 | Jackson |
| 2013/0312188 A1 | 11/2013 | Jackson |
| 2013/0318721 A1* | 12/2013 | Gauta ................. A61G 13/125 5/624 |
| 2013/0338792 A1 | 12/2013 | Schmieding et al. |
| 2013/0345605 A1 | 12/2013 | Steele |
| 2014/0020181 A1 | 1/2014 | Jackson |
| 2014/0033434 A1 | 2/2014 | Jackson |
| 2014/0068863 A1 | 3/2014 | Clark et al. |
| 2014/0068866 A1 | 3/2014 | Catacchio et al. |
| 2014/0082842 A1 | 3/2014 | Jackson |
| 2014/0173827 A1 | 6/2014 | Hiebert |
| 2014/0174451 A1 | 6/2014 | Hiebert |
| 2014/0196212 A1 | 7/2014 | Jackson |
| 2014/0201913 A1 | 7/2014 | Jackson |
| 2014/0201914 A1 | 7/2014 | Jackson |
| 2014/0208512 A1 | 7/2014 | Jackson |
| 2014/0208513 A1 | 7/2014 | Hiebert |
| 2014/0215718 A1 | 8/2014 | Wootton |
| 2014/0215855 A1 | 8/2014 | Frey |
| 2014/0222407 A1 | 8/2014 | Jordan et al. |
| 2014/0283845 A1* | 9/2014 | Slusarz, Jr. ............ A61B 5/055 128/845 |
| 2014/0309646 A1 | 10/2014 | Fan et al. |
| 2014/0317847 A1 | 10/2014 | Jackson |
| 2014/0324056 A1 | 10/2014 | Nikolchev et al. |
| 2014/0359941 A1 | 12/2014 | Sharps et al. |
| 2014/0366271 A1 | 12/2014 | Marshall |
| 2015/0008201 A1 | 1/2015 | Qiang et al. |
| 2015/0032041 A1* | 1/2015 | Ingimundarson ..... A61F 5/0111 602/27 |
| 2015/0059094 A1 | 3/2015 | Jackson |
| 2015/0067985 A1 | 3/2015 | Gaenzle |
| 2015/0088044 A1 | 3/2015 | Walborn |
| 2015/0122268 A1 | 5/2015 | Slusarz, Jr. |
| 2015/0150743 A1 | 6/2015 | Jackson |
| 2015/0164724 A1 | 6/2015 | Drake et al. |
| 2015/0196447 A1 | 7/2015 | Henderson et al. |
| 2015/0202106 A1 | 7/2015 | Hight et al. |
| 2015/0231013 A1 | 8/2015 | Bernardoni et al. |
| 2015/0238273 A1 | 8/2015 | Jordan et al. |
| 2015/0238380 A1 | 8/2015 | Kreuzer et al. |
| 2015/0245915 A1 | 9/2015 | Crabtree, Jr. et al. |
| 2015/0245969 A1 | 9/2015 | Hight et al. |
| 2015/0245971 A1 | 9/2015 | Bernardoni et al. |
| 2015/0272681 A1 | 10/2015 | Skripps et al. |
| 2015/0290064 A1* | 10/2015 | Kreuzer ................... A61F 5/04 128/845 |
| 2015/0297435 A1 | 10/2015 | Visco |
| 2015/0342813 A1 | 12/2015 | Catacchio et al. |
| 2015/0366622 A1 | 12/2015 | Wyslucha et al. |
| 2016/0008201 A1 | 1/2016 | Jackson et al. |
| 2016/0038364 A1 | 2/2016 | Jackson |
| 2016/0051432 A1 | 2/2016 | Clark et al. |
| 2016/0067135 A1 | 3/2016 | Pigazzi et al. |
| 2016/0095784 A1 | 4/2016 | Catacchio et al. |
| 2016/0095785 A1 | 4/2016 | Catacchio et al. |
| 2016/0106612 A1 | 4/2016 | Clark et al. |
| 2016/0120720 A1 | 5/2016 | Hirsch |
| 2016/0120726 A1 | 5/2016 | Moriarty et al. |
| 2016/0184154 A1 | 6/2016 | Lafleche et al. |
| 2016/0228281 A1 | 8/2016 | Marshall et al. |
| 2016/0279007 A1 | 9/2016 | Flatt |
| 2016/0317237 A1 | 11/2016 | Geiger |
| 2016/0338691 A1 | 11/2016 | Weber et al. |
| 2016/0354223 A1* | 12/2016 | Burns .................. A61F 5/0123 |

FOREIGN PATENT DOCUMENTS

| | | |
|---|---|---|
| DE | 20 2012 101 347 | 8/2012 |
| DE | 10 2011 016 456 | 2/2016 |
| EP | 2 574 325 | 4/2013 |
| EP | 2 623 082 | 8/2013 |
| EP | 2 618 313 | 7/2014 |
| EP | 2 873 405 | 5/2015 |
| EP | 2 982 880 | 2/2016 |
| EP | 2 802 305 | 10/2018 |

(56) References Cited

FOREIGN PATENT DOCUMENTS

| WO | WO 03/061544 | 7/2003 |
|---|---|---|
| WO | WO 2006/091239 | 8/2006 |
| WO | WO 2007/021806 | 2/2007 |
| WO | WO 2007/080454 | 7/2007 |
| WO | WO 2008/150731 | 12/2008 |
| WO | WO 2009/062324 | 5/2009 |
| WO | WO 2013/034916 | 3/2013 |
| WO | WO 2014/043538 | 3/2014 |
| WO | WO 2014/045194 | 3/2014 |
| WO | WO 2014/045199 | 3/2014 |
| WO | WO 2014/153329 | 9/2014 |
| WO | WO 2014/205218 | 12/2014 |
| WO | WO 2016/017479 | 2/2016 |
| WO | WO 2016/197142 | 12/2016 |

OTHER PUBLICATIONS

Kollmorgen, Robert C., The Pink Hip Kit®: Postless Hip Arthroscopy Positioning System, Xodus Medical.

Mei-Dan, O. et al. Hip Arthroscopy Distraction Without the Use of Perineal Post: Prospective Study (Abstract), vol. 36, No. 1, Jan. 2013, pp. e1-e5.

Opfell, A., Hip Arthroscopy & Fracture Kit: Maximize patient safety during arthroscopic hip procedures, Xodus Medical, Jul. 12, 2018.

Pink Pad—Advanced Trendelenburg Positioning System, Xodus Medical Inc., 2018, https://www.xodusmedical.com/pinkpad.

Steep Trendelenburg Positioners, Prime Medical LLC, 2019, http://primemedicalllc.com/steep-trendelenburg-positioners/.

Terry, M.A., Arthroscopic Hip Patient Positioning Using the Advanced Supine Hip Positioning System: Hip Technique Guide, Smith & Nephew, 2013, pp. 1-8.

Harris, The Pink Hip Kit SN: Postless Positioning System—HIP40614SN, Xodus Medical, 2019.

Harris, The Pink Hip Kit SN: Postless Poitioning System—72205286, Xodus Medical, 2019, https://www.xodusmedical.com/Product/HIP40614SN.

The Pink Pad XL®: Advanced Trendelenburg Positioning System, Xodus Medical, 2018.

Trendelenburg Positioning Kits, Soule Medical, 2018, https://www.soulemedical.com/index.php/trendelenburg-positioning-kit.

Young, D.A et al., Technique allows for hip arthoscopy distraction without perineal post, Orthopedics Today, Jun. 2013, https://www.healio.com/orthopedics/arthroscopy/news/print/orthopedics-today/%7Bac540b4c-9b43-4736-ae8a-606b1457af8b%7D/technique-allows-for-hip-arthroscopy-distraction-without-perineal-post.

Hip Arthroscopy and Fracture Kit, SPK10246—Hip Arthroscopy and Fracture Kit with Perineal Post Cover.

* cited by examiner

ANATOMICAL GRIPPING SYSTEM FOR GRIPPING THE LEG AND FOOT OF A PATIENT WHEN EFFECTING HIP DISTRACTION AND/OR WHEN EFFECTING LEG POSITIONING

REFERENCE TO PENDING PRIOR PATENT APPLICATIONS

This patent application claims benefit of:

(i) prior U.S. Provisional Patent Application Ser. No. 62/455,154, filed Feb. 6, 2017 by Stryker Corp. and William Kaiser et al. for ANATOMICAL GRIPPING SYSTEM; and (ii) prior U.S. Provisional Patent Application Ser. No. 62/546,629, filed Aug. 17, 2017 by Stryker Corp. and William Kaiser et al. for ANATOMICAL GRIPPING SYSTEM FOR GRIPPING THE LEG OF A PATIENT WHEN EFFECTING HIP DISTRACTION OR LEG POSITIONING.

The two (2) above-identified patent applications are hereby incorporated herein by reference.

FIELD OF THE INVENTION

This invention relates to medical apparatus in general, and more particularly to medical apparatus for gripping the leg and foot of a patient when effecting hip distraction and/or when effecting leg positioning.

BACKGROUND OF THE INVENTION

When performing surgical procedures on the hip joint, it is common to distract the hip joint prior to the surgery so as to provide additional room within the joint and so as to better present selected anatomy to the surgeon. This hip distraction is commonly achieved by applying a distraction force to the distal end of the leg of the patient. The distraction force applied to the distal end of the leg of the patient is typically around 50-100 pounds (or more) of force. Currently, a surgical boot is placed on the foot and lower leg of the patient, the surgical boot is connected to a distraction frame, and then the distraction frame is used to apply a distraction force to the boot, whereby to apply a distraction force to the leg of the patient. Securing the leg of the patient to the distraction frame also allows for appropriate positioning of the leg of the patient during various surgical procedures (e.g., such as when placing the leg into abduction).

Unfortunately, in many cases, the foot and lower leg of the patient (and particularly the heel of the patient) can slip within the surgical boot when the distraction force is applied, thereby reducing the amount of distraction achieved. This is particularly true with patients who have small feet and wide ankles, since this makes it difficult to secure the patient's anatomy within the surgical boot. Such slippage of the anatomy within the surgical boot can be highly problematic, since the amount of hip distraction achieved is typically fairly small to begin with, and hence any slippage of the anatomy within the surgical boot can further reduce the amount of hip distraction achieved. In addition, when the anatomy of the patient slips within the surgical boot, the points of engagement between the surgical boot and the anatomy shift, such that the anatomy may be out of position within the surgical boot and/or the anatomy may no longer be properly oriented relative to the distraction frame. For this reason, many surgeons personally strap the patient's foot and lower leg into the surgical boot in an effort to ensure that the foot and lower leg of the patient are secured to the maximum extent possible within the surgical boot. It is also common for surgeons to augment the fit of the surgical boot with extra tape, bandages and/or padding in order to minimize slippage within the surgical boot.

SUMMARY OF THE INVENTION

The present invention provides a new and improved approach for securing the leg of a patient to a distraction frame, wherein the conventional surgical boot is replaced by a novel anatomical gripping system which eliminates the problems associated with conventional surgical boots.

In one form of the invention, there is provided an anatomical gripping system comprising:

a binding comprising:
   a substantially rigid spine;
   a calf shell mounted to the substantially rigid spine;
   an anterior shell; and
   a clamping mechanism connecting the anterior shell to the calf shell;
   wherein the calf shell comprises a flexible portion configured to selectively engage the superior portion of the calcaneus bone of a patient;
   and further wherein when the clamping mechanism applies a force to the flexible portion of the calf shell, the flexible portion of the calf shell is drawn into engagement with the superior portion of the calcaneus bone of the patient.

In another form of the invention, there is provided a method for distracting a hip joint, the method comprising:
   providing an anatomical gripping system comprising:
      a binding comprising:
         a substantially rigid spine;
         a calf shell mounted to the substantially rigid spine;
         an anterior shell; and
         a clamping mechanism connecting the anterior shell to the calf shell;
         wherein the calf shell comprises a flexible portion configured to selectively engage the superior portion of the calcaneus bone of a patient;
         and further wherein when the clamping mechanism applies a force to the flexible portion of the calf shell, the flexible portion of the calf shell is drawn into engagement with the superior portion of the calcaneus bone of the patient;
   positioning the patient's foot and lower leg in the binding;
   using the clamping mechanism to apply a force to the flexible portion of the calf shell so that the flexible portion of the calf shell is drawn into engagement with the superior portion of the calcaneus bone of the patient; and
   applying a distracting force to the substantially rigid spine of the binding.

In another form of the invention, there is provided an anatomical gripping system comprising:

a soft wrap for covering at least a portion of a patient's lower leg superior to the malleoli bones while not covering the bony prominence of the malleoli bones; and a binding comprising:
   a substantially rigid spine;
   a calf shell mounted to the substantially rigid spine;
   an anterior shell; and
   a clamping mechanism connecting the anterior shell to the calf shell;
   such that when the clamping mechanism applies a clamping force between the anterior shell and the calf shell, the clamping force is directed onto the soft wrap covering at least a portion of the patient's lower leg superior to the malleoli bones.

In another form of the invention, there is provided a method for distracting a hip joint, the method comprising:
providing an anatomical gripping system comprising:
a soft wrap for covering at least a portion of a patient's lower leg above the malleoli bones while not covering the bony prominence of the malleoli bones; and
a binding comprising:
a substantially rigid spine;
a calf shell mounted to the substantially rigid spine;
an anterior shell; and
a clamping mechanism connecting the anterior shell to the calf shell;
such that when the clamping mechanism applies a clamping force between the anterior shell and the calf shell, the clamping force is directed onto the soft wrap covering at least a portion of the patient's lower leg above the malleoli bones;
positioning the patient's foot and lower leg in the binding;
using the clamping mechanism to apply a clamping force between the anterior shell and the calf shell, such that the clamping force is directed onto the soft wrap covering at least a portion of the patient's lower leg above the malleoli bones; and
applying a distracting force to the substantially rigid spine of the binding.

In another form of the invention, there is provided an anatomical gripping system comprising:
a binding comprising:
a substantially rigid spine;
a calf shell mounted to the substantially rigid spine;
an anterior shell; and
at least two clamping mechanisms connecting the anterior shell to the calf shell;
wherein the at least two clamping mechanisms apply clamping forces between the anterior shell and the calf shell;
and further wherein the anterior shell comprises reduced width between the at least two clamping mechanisms so as to provide the anterior shell with increased flexibility for conforming to the anatomy of a patient.

In another form of the invention, there is provided a method for distracting a hip joint, the method comprising:
providing an anatomical gripping system comprising:
a binding comprising:
a substantially rigid spine;
a calf shell mounted to the substantially rigid spine;
an anterior shell; and
at least two clamping mechanisms connecting the anterior shell to the calf shell;
wherein the at least two clamping mechanisms apply clamping forces between the anterior shell and the calf shell;
and further wherein the anterior shell comprises reduced width between the at least two clamping mechanisms so as to provide the anterior shell with increased flexibility for conforming to the anatomy of a patient;
positioning the patient's foot and lower leg in the binding;
using the at least two clamping mechanisms to apply a clamping force between the anterior shell and the calf shell, such that the clamping force is directed onto the anatomy of a patient; and
applying a distracting force to the substantially rigid spine of the binding.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein.

DETAILED DESCRIPTION OF THE PREFERRED EMBODIMENTS

The present invention provides a new and improved approach for securing the leg of a patient to a distraction frame, wherein the conventional surgical boot is replaced by a novel anatomical gripping system which eliminates the problems associated with conventional surgical boots.

Figure 1:
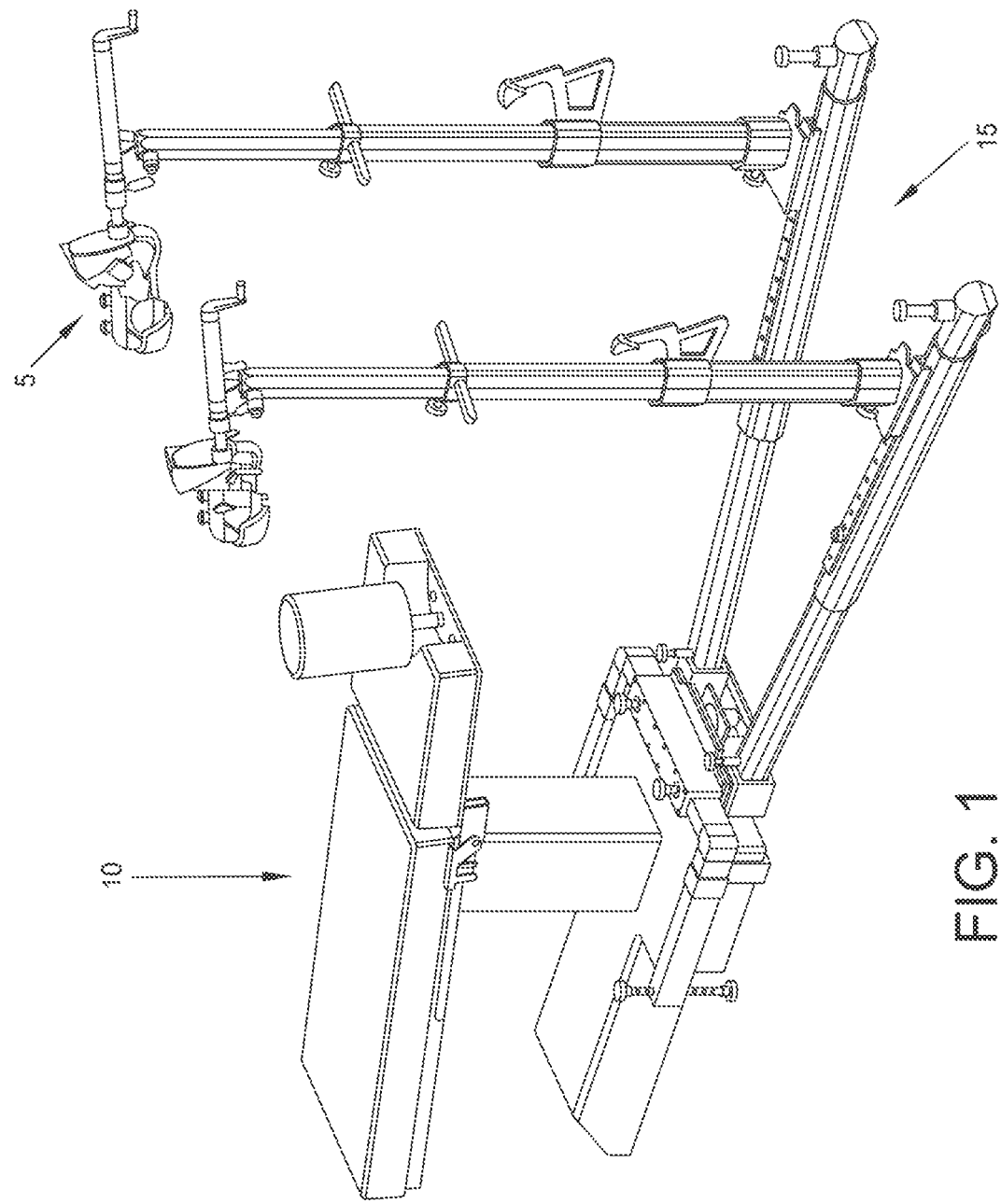
FIG. 1 is a schematic view showing a surgical table, a distraction frame, and portions of a novel anatomical gripping system formed in accordance with the present invention.

More particularly, and looking first at FIG. 1, the present invention comprises a novel anatomical gripping system 5 formed in accordance with the present invention. Anatomical gripping system 5 is intended to grip the foot and lower leg of a patient lying on a surgical table 10, with anatomical gripping system 5 being connected to a distraction frame 15, such that distraction frame 15 can apply a distraction force to the leg of a patient via anatomical gripping system 5.

Anatomical Gripping System 5 in General

Figure 2:
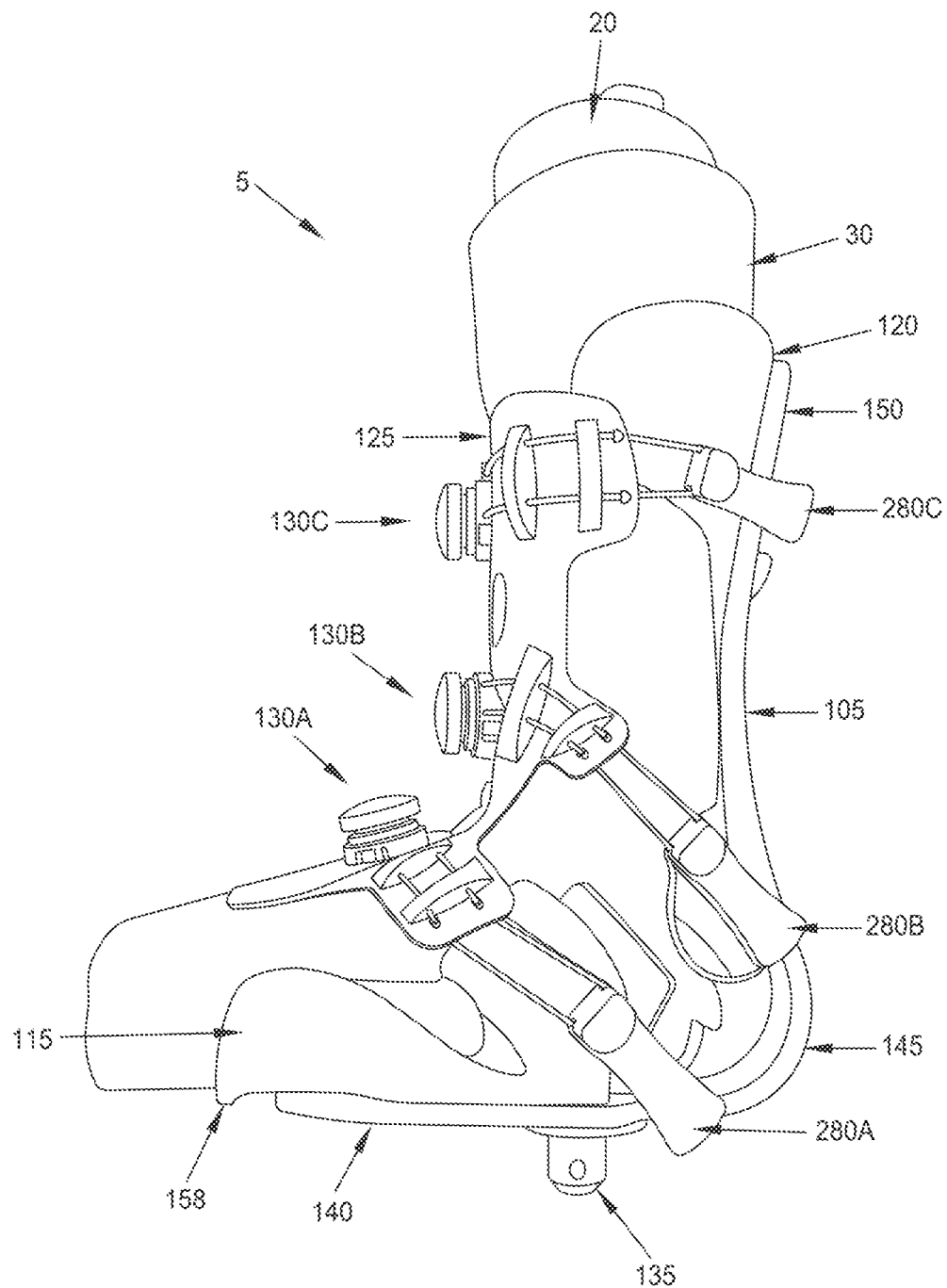
FIGS. 2-4 are schematic views showing a novel anatomical gripping system formed in accordance with the present invention.
Figure 3:
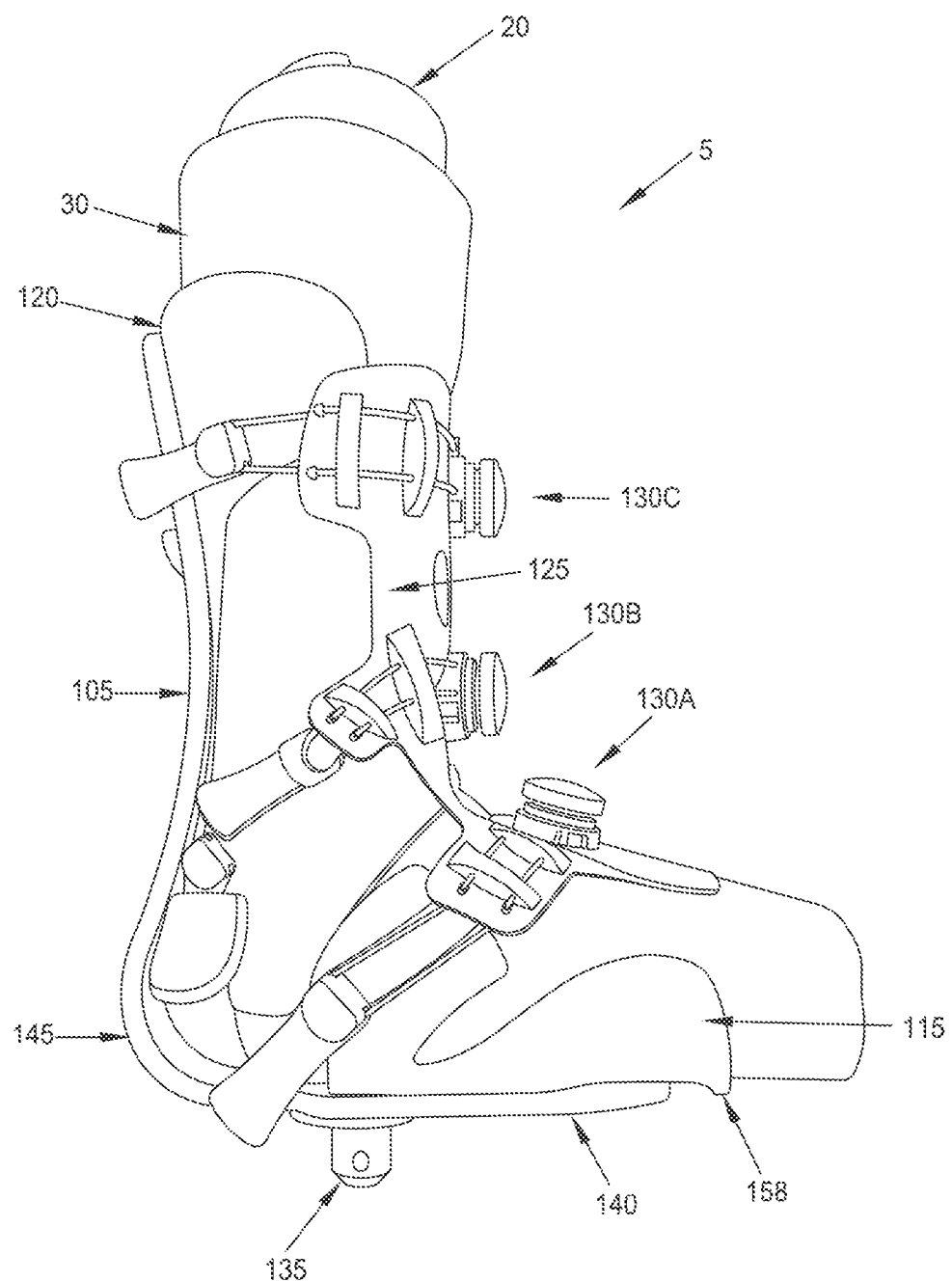
Figure 4:
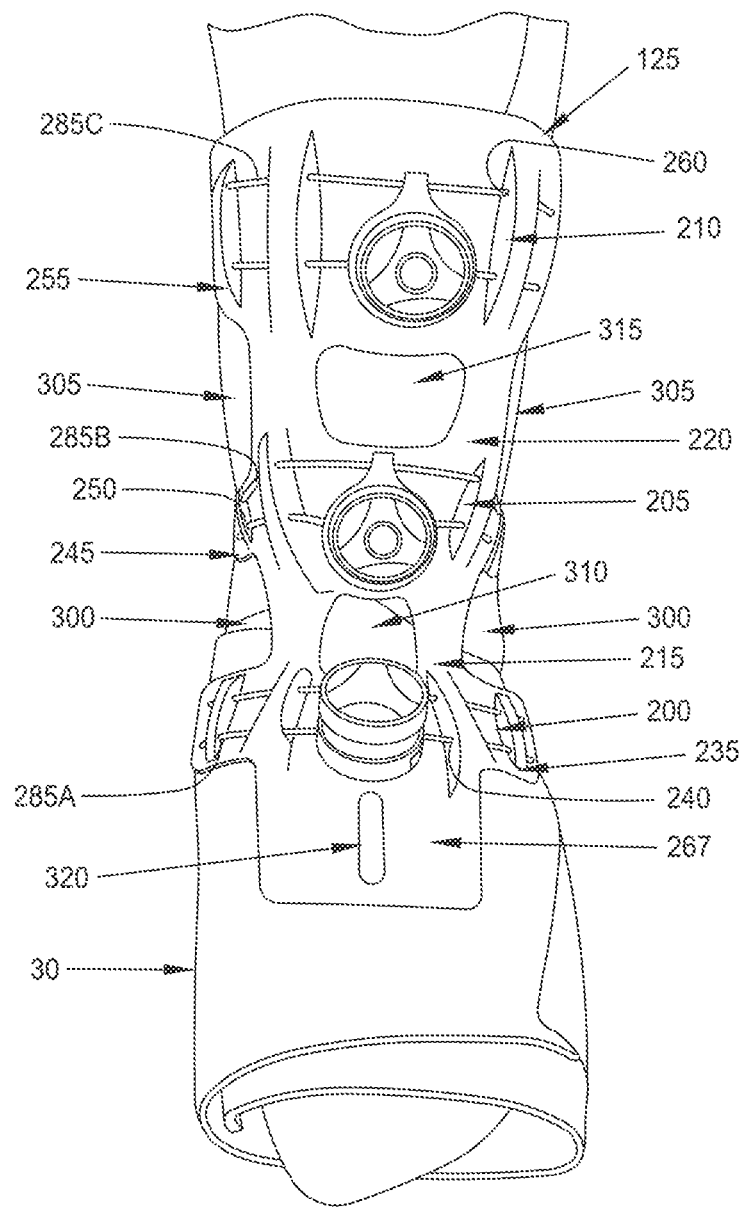

Anatomical gripping system 5 is shown gripping a simulation leg 20 in FIGS. 2-4. As will hereinafter be discussed, anatomical gripping system 5 comprises various components which are designed to optimize the manner in which anatomical gripping system 5 grips the foot and lower leg of a patient. Significantly, this results in enhanced gripping of the anatomy by anatomical gripping system 5, and less slippage of the anatomy relative to anatomical gripping system 5, particularly with respect to slippage of the heel of the patient relative to anatomical gripping system 5.

Figure 5:
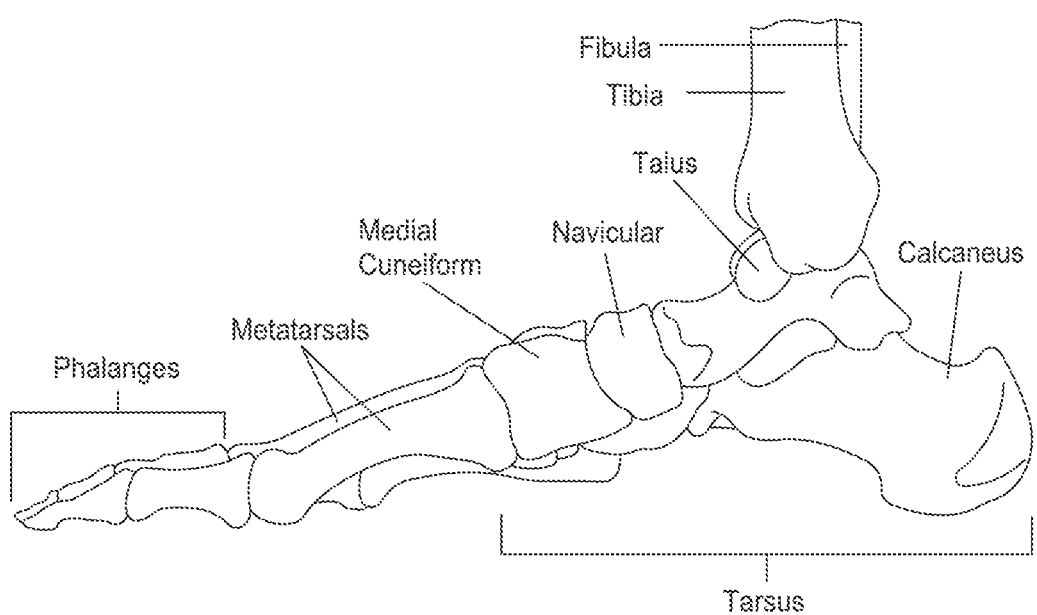
FIGS. 5 and 6 are schematic views showing some of the bones of the foot and lower leg of a human.
Figure 6:
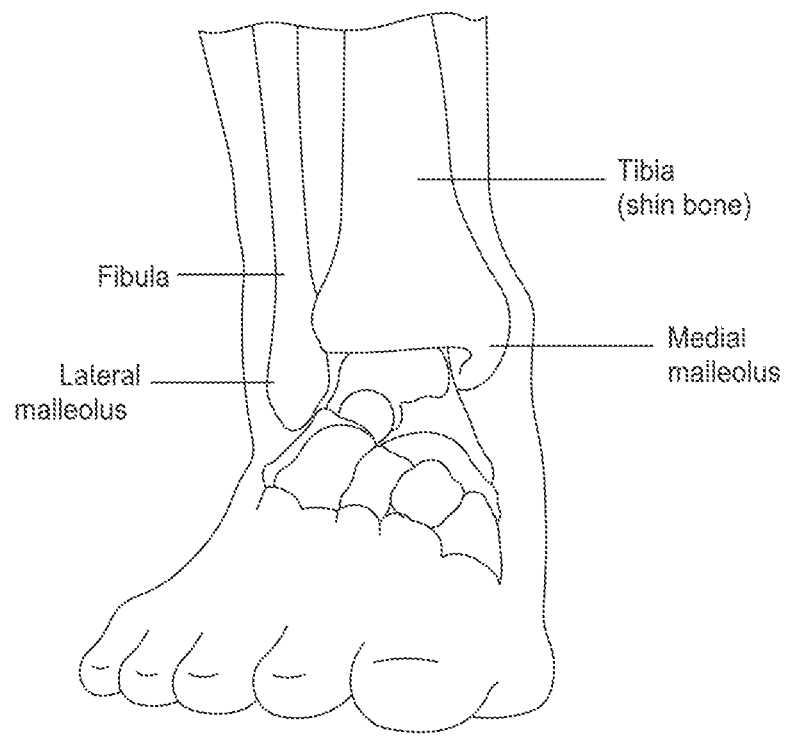
Figure 7:
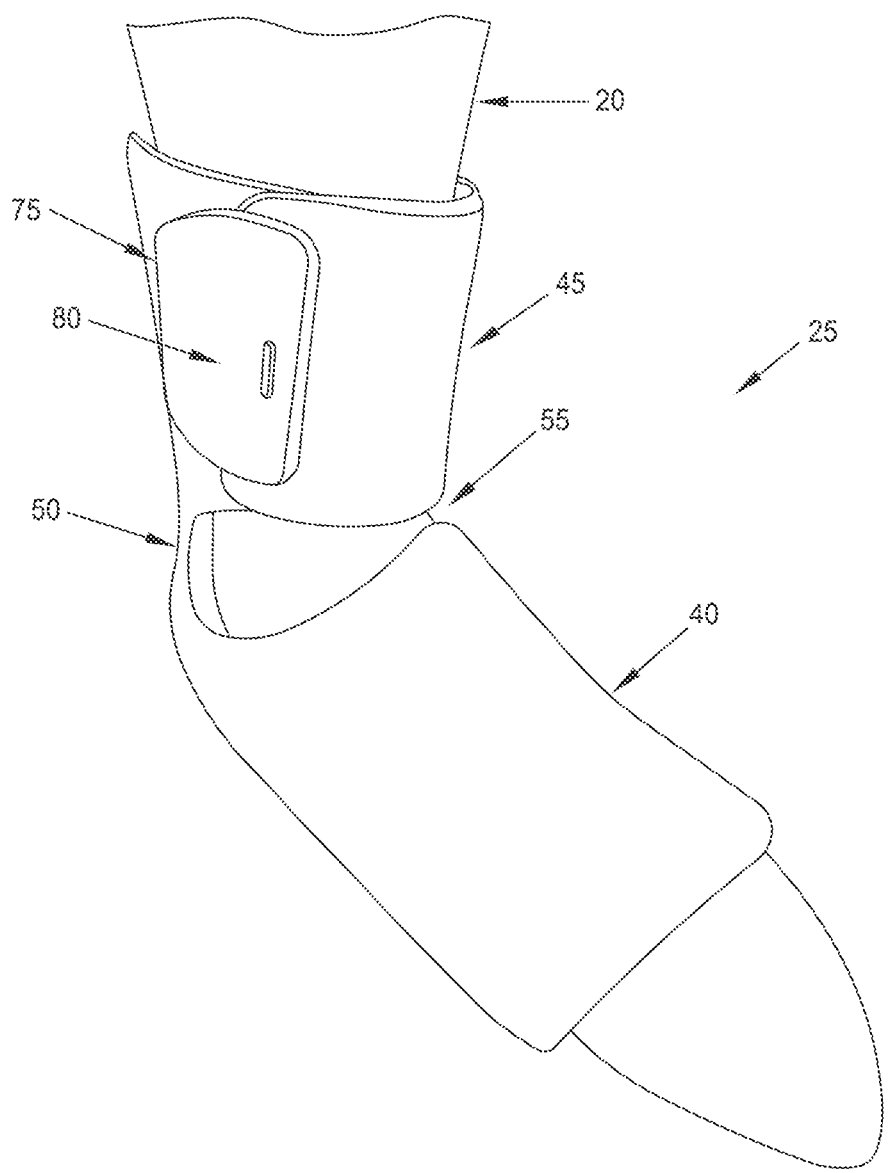
FIGS. 7, 7A, 8 and 9 are schematic views showing further details of the soft butterfly wrap of the novel anatomical gripping system of the present invention.
Figure 7A:
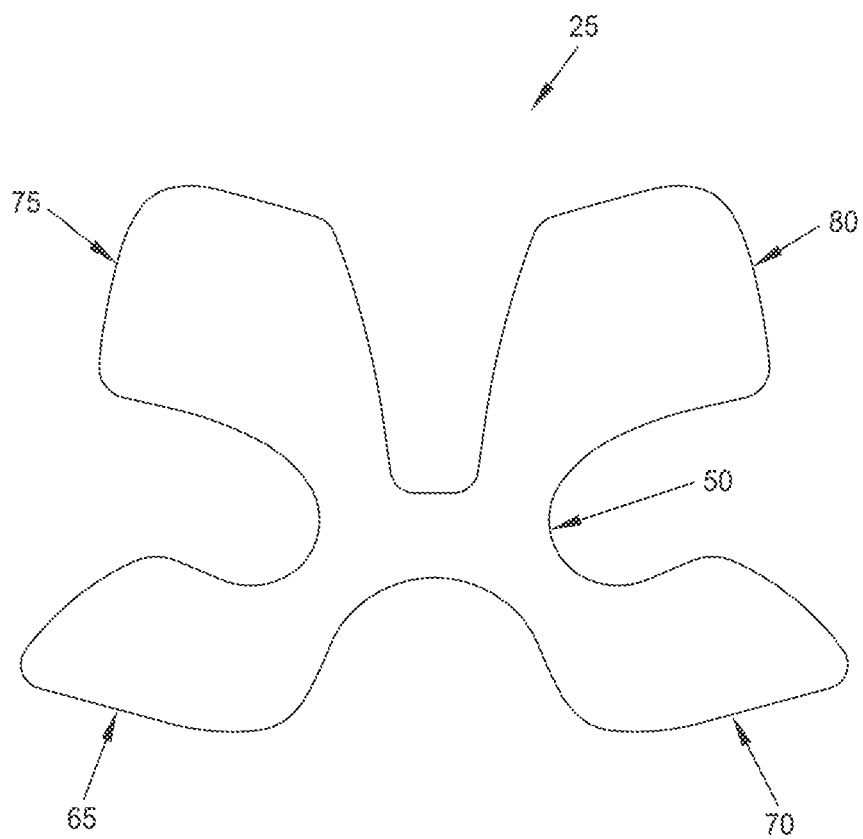
Figure 8:
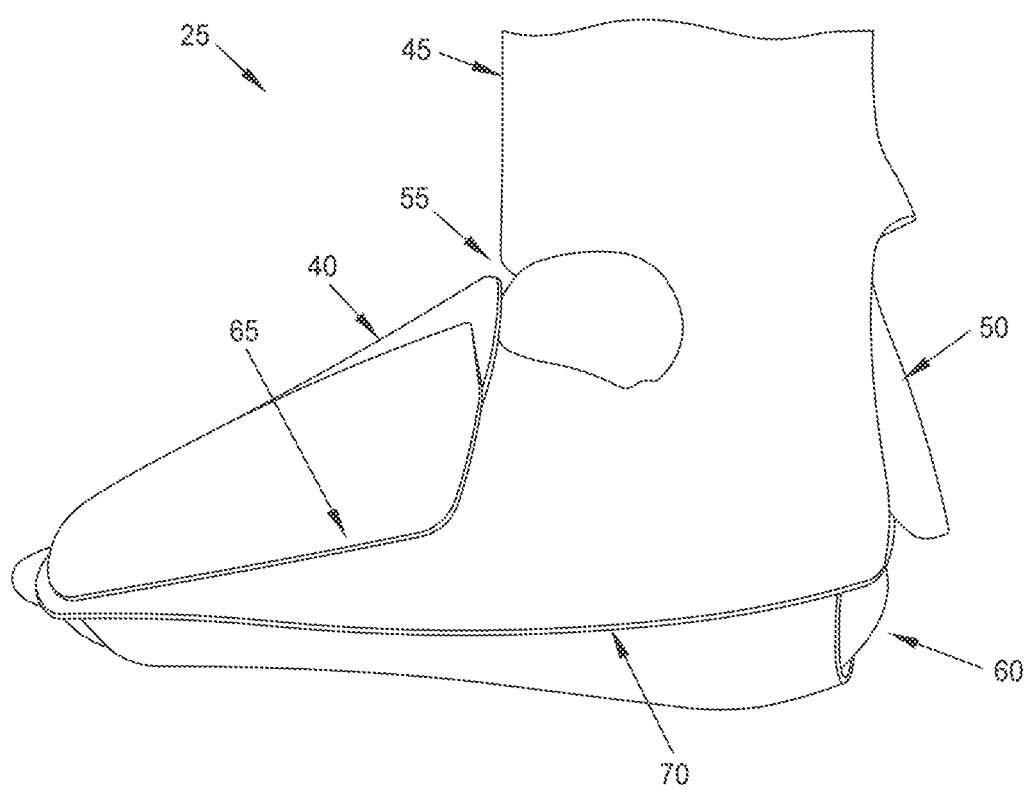
Figure 9:
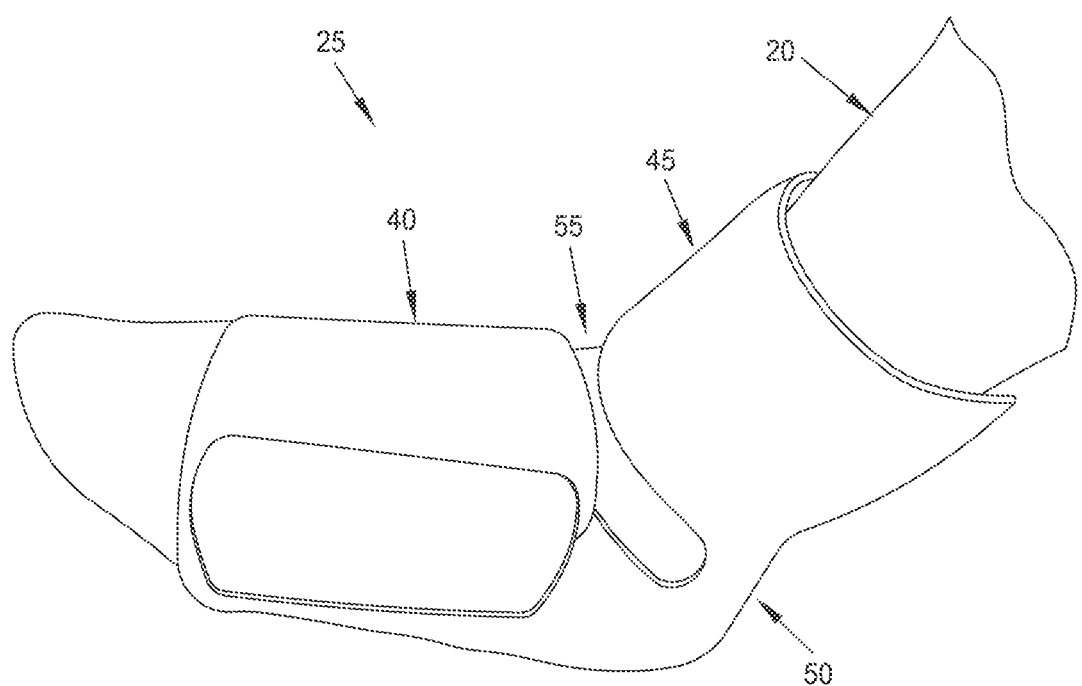
Figure 9A:
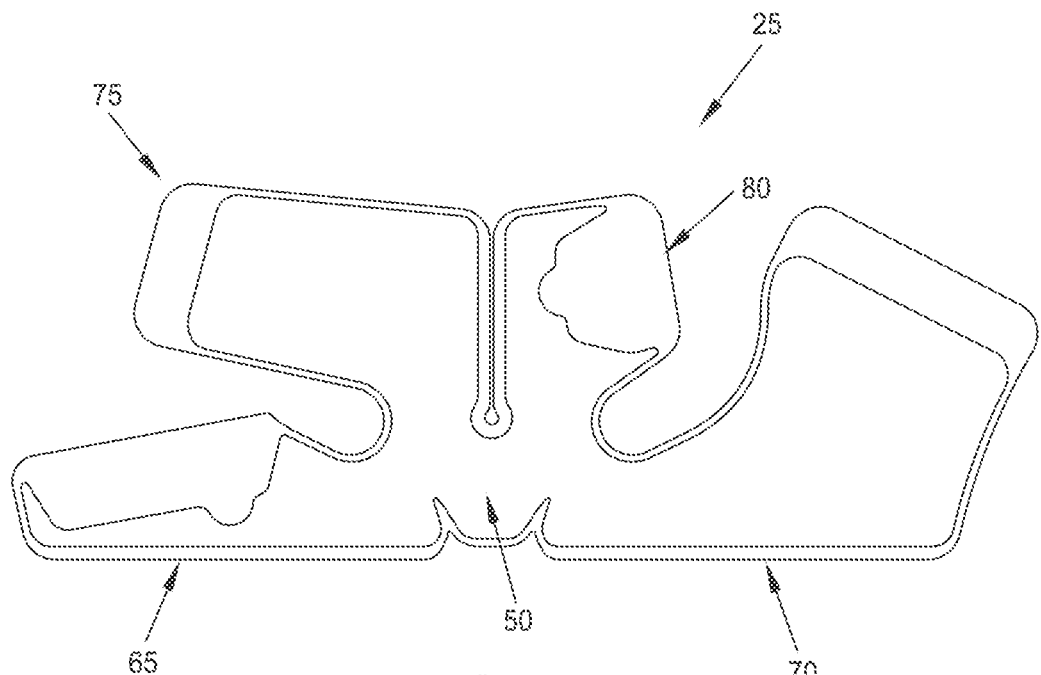
FIGS. 9A-9D are schematic views showing another soft butterfly wrap of the novel anatomical gripping system of the present invention.
Figure 9B:
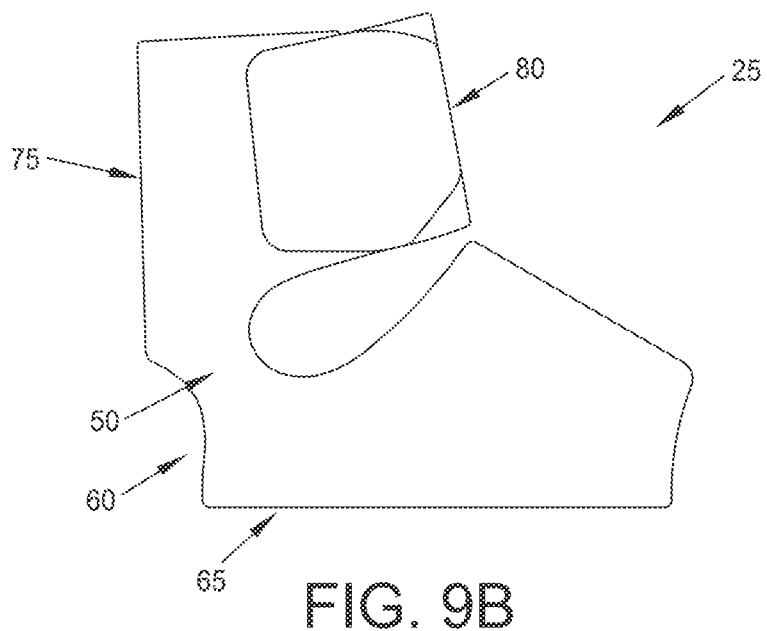
Figure 9D:
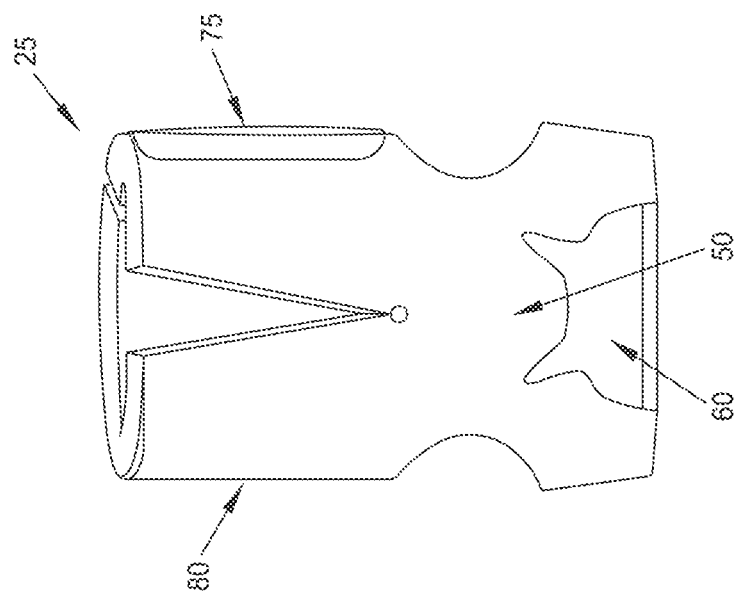
Figure 9C:
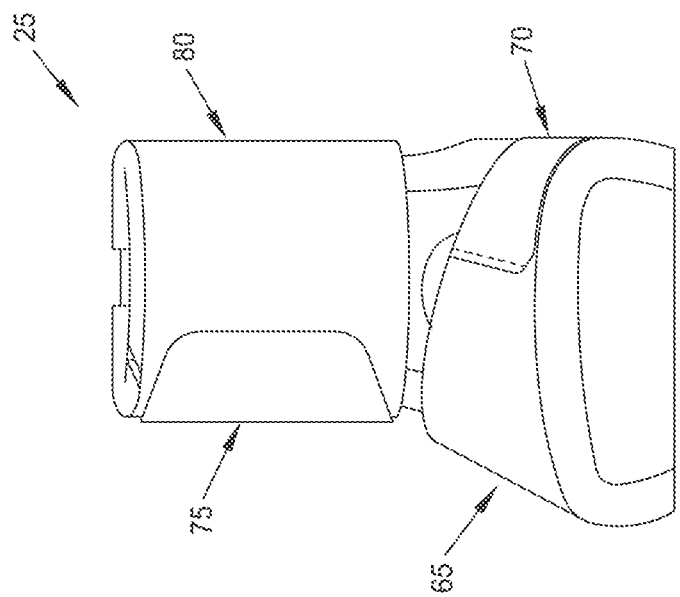

More particularly, FIGS. 5 and 6 show some of the bones of the foot and lower leg of a human. In accordance with the present invention, and as will hereinafter be discussed in further detail, anatomical gripping system 5 is designed to grip the foot of the patient at the forefoot and at the calcaneus bone, i.e., on the superior (i.e., proximal) surface of the calcaneus bone (FIGS. 5 and 10), and to grip the leg of the patient superior at the malleoli, i.e., on the superior (i.e., proximal) surface of the lateral malleolus of the fibula and on the superior (i.e., proximal) surface of the medial malleolus of the tibia (FIGS. 6 and 10) (as used herein, the terms "superior to" and "proximal to" are intended to be understood as being in the cephalad direction on a patient, and "inferior to" and "distal to" are intended to be understood as being in the caudal direction on a patient).

Significantly, and as will hereinafter be discussed, anatomical gripping system 5 is designed to securely grip the essential anatomy of the patient without requiring adjacent non-essential anatomy to be tightly squeezed, thus reducing the pressure that the remaining surfaces of the foot and lower leg receive. Gripping the foot and lower leg of the patient using the prominent bones of the foot and lower leg of the patient (i.e., the calcaneus and malleoli bones) ensures a secure grip of the foot and lower leg of the patient while minimizing trauma to the anatomy of the patient. This approach is in sharp contrast to the approach of conventional surgical boots, which seek to tighten down the surgical boot across the dorsum of the foot and about the ankle of the patient, in a relatively focal zone which contains soft tissue, nerves and blood supply. The use of conventional surgical boots can lead to injury if the surgical boot is excessively tightened, but can also lead to slippage if the surgical boot is not sufficiently tightened.

Additionally, conventional surgical boots generally hold the foot of a patient at a 90 degree angle relative to the lower leg of the patient. While this disposition of the foot relative to the lower leg of the patient may be appropriate for footwear of the sort used for walking, it is not necessarily optimal for gripping the foot and lower leg of the patient for hip distraction purposes. By contrast, and as will hereinafter be discussed, the present invention may be configured to hold the foot of the patient at an angle of approximately 100 degrees relative to the lower leg of the patient. Inclining the foot of the patient at an angle of approximately 100 degrees relative to the lower leg of the patient places the calcaneus bone in a more pronounced position and thus allows for significantly improved gripping of the foot and lower leg of the patient by anatomical gripping system 5. The aforementioned approximately 100 degree incline between the foot of the patient and the lower leg of the patient may also provide the additional benefit of greater comfort for the patient. Note that, if desired, the angle of incline between the foot and lower leg of the patient may also be greater than approximately 100 degrees in order to allow for more flex of the foot. Note also that, if desired, the angle of incline between the foot and lower leg of the patient may be less than approximately 100 degrees, but preferably is not less than approximately 90 degrees.

In accordance with the present invention, anatomical gripping system 5 generally comprises three components:
  (i) a soft butterfly wrap 25 (FIGS. 7, 7A and 8-11);
  (ii) a soft liner 30 (FIGS. 2-4, 10-12, 12A, 12B, 13 and 13A); and
  (iii) a binding 35 (FIGS. 2-4, 10 and 14-34).

A. Soft Butterfly Wrap 25

Soft butterfly wrap 25 (FIGS. 7, 7A and 8-11) is intended to be positioned directly against the skin of the patient on both sides of the malleoli. Soft butterfly wrap 25 is preferably formed out of a foam of density and stiffness similar to what may be seen in performance sports footwear like ski boots, snow board boots and skates. The foam serves to "build up" the anatomy of the patient distal (i.e., inferior) to the malleoli and proximal (i.e., superior) to the malleoli, whereby to facilitate gripping the anatomy of the patient both distal (i.e., inferior) and proximal (i.e., superior) to the malleoli, and whereby to facilitate distributing the gripping load imposed on the anatomy of the patient.

More particularly, soft butterfly wrap 25 comprises a lower band 40, an upper band 45 and a connecting portion 50. Lower band 40 surrounds the mid-foot and forefoot of the patient. Upper band 45 surrounds the lower leg proximal (i.e., superior) to the malleoli. Connecting portion 50 connects lower band 40 of soft butterfly wrap 25 with upper band 45 of soft butterfly wrap 25. Note that a gap 55 is formed between lower band 40 and upper band 45, with gap 55 including the region over the malleoli. Note also that an opening 60 is formed distal (i.e., inferior) to connecting portion 50 in the region of the heel of the patient. Thus, soft butterfly wrap 25 does not cover the heel of the patient or otherwise engage the heel of the patient. This is to allow the surgical staff to visualize or measure the spacing of the heel of the patient from binding 35 (see below).

In one form of the invention, lower band 40 is formed by two straps 65, 70 which are adjustably connectable to one another (e.g., via hook-and-loop fasteners) so as to form the complete lower band 40, and upper band 45 is formed by two straps 75, 80 which are adjustably connectable to one another (e.g., via hook-and-loop fasteners) so as to form the complete upper band 45. Alternatively, one or both of lower band 40 and upper band 45 may comprise a sleeve which encircles the foot (lower band 40) or leg (upper band 45) for disposition about the anatomy of the patient, wherein the sleeve comprises an elastic material so as to allow the sleeve to closely conform to the anatomy of the patient.

If desired, the interior surfaces of soft butterfly wrap 25 may at least partially comprise a high friction material (e.g., silicone rubber). The inclusion of this high friction material increases the gripping action between soft butterfly wrap 25 and the foot and lower leg of the patient.

FIGS. 9A-9D show another soft butterfly wrap 25 also formed in accordance with the present invention.

B. Soft Liner 30

Soft liner 30 (FIGS. 2-4, 10-12, 12A, 12B, 13 and 13A) is intended to be draped over the foot and calf of the patient (and over soft butterfly wrap 25) so as to provide protective and hygienic coverage for the distal end of the patient's leg. Soft liner 30 preferably comprises an opening 82 (see FIG. 13) in the region of the heel of the patient so that soft liner 30 does not cover the heel of the patient or otherwise engage the heel of the patient. This is to allow the surgical staff to visually examine the position of the patient's heel within binding 35, particularly during leg distraction, and particularly for the purpose of checking for undesired heel lift during leg distraction (or other leg positioning). Additionally, soft liner 30 does not cover the toes of the patient (see, for example, FIG. 12). This is so that the surgical staff can examine the toes of the patient during the surgical procedure (e.g., so as to ensure that the toes of the patient have adequate blood circulation).

In one form of the invention, soft liner 30 is formed by four segments 85, 90, 95, 100, with segments 85, 90 being adjustably connectable to one another (e.g., via hook-and-loop fasteners) so as to cover a portion of the foot of the patient (and so as to cover lower band 40 of soft butterfly wrap 25), and with segments 95, 100 being adjustably connectable to one another (e.g., via hook-and-loop fasteners) so as to cover a portion of the leg of the patient (and so as to cover upper band 45 of soft butterfly wrap 25). In one form of the invention, and looking now at FIGS. 12A and 12B, soft liner 30 may comprise two panels 101, 102, where panel 101 comprises the aforementioned segments 85 and 90, and where panel 102 comprises the aforementioned segments 95 and 100, with panels 101, 102 being sewn together at sew tabs 103.

Alternatively, soft liner 30 may comprise a sleeve for disposition around the anatomy of the patient, wherein the sleeve comprises an elastic material so as to allow the sleeve to closely conform to the anatomy of the patient.

If desired, the interior surfaces of soft liner 30 may at least partially comprise a high friction material (e.g., silicone rubber). The inclusion of this high friction material increases the gripping action between soft liner 30 and soft butterfly wrap 25, and increases the gripping action between soft liner 30 and the foot and lower leg of the patient.

In addition, if desired, the exterior surfaces of soft liner 30 may at least partially comprise a high friction material (e.g., silicone rubber). The inclusion of this high friction material increases the gripping action between soft liner 30 and binding 35.

If desired, soft butterfly wrap 25 and soft liner 30 may be formed as two separate components, and they may be applied to the patient in two distinct steps, i.e., first soft butterfly wrap 25 is applied to the patient, and then soft liner 30 is applied to the patient (and over soft butterfly wrap 25). More preferably, however, and looking now at FIG. 13A, soft butterfly wrap 25 and soft liner 30 are provided as a singular construction (e.g., soft butterfly wrap 25 is secured to soft liner 30 at the time of manufacture). This singular construction may be effected by simply attaching soft butterfly wrap 25 to soft liner 30, or by incorporating the features of both components (i.e., soft butterfly wrap 25 and soft liner 30) in a single modified construction.

C. Binding 35

Binding 35 (FIGS. 2-4, 10 and 14-34) is intended to be positioned over soft butterfly wrap 25 and soft liner 30 after soft butterfly wrap 25 and soft liner 30 have been positioned on the foot and lower leg of the patient, and then binding 35 is intended to be secured to the foot and lower leg of the patient, such that binding 35 can thereafter be used to secure the leg of the patient to distraction frame 15.

Binding 35 generally comprises a long, narrow spine 105, a plantar shell 115, a calf shell 120, an anterior shell 125 and three cable assemblies 130A, 130B and 130C.

(i) Long, Narrow Spine 105

Long, narrow spine 105 (FIGS. 2, 3, 10 and 19-24) extends from approximately the arch of the foot of the patient to the calf of the patient, and includes a mount 135 (FIG. 2) for mounting long, narrow spine 105 to distraction frame 15.

More particularly, long, narrow spine 105 comprises a plantar portion 140, a curved portion 145 and a calf portion 150. Plantar portion 140 is preferably set at an angle of approximately 100 degrees relative to calf portion 150 so as to place the calcaneus bone in a more pronounced position when the foot and lower leg of the patient are gripped by anatomical gripping system 5, whereby to provide improved gripping of the anatomy of the patient, and so as to provide increased comfort for the patient. Curved portion 145 curves away from the heel of the patient (see FIGS. 2 and 3) so as to allow the surgical staff to visualize or measure the spacing of the heel of the patient from long, narrow spine 105.

(ii) Plantar Shell 115

Figure 21:
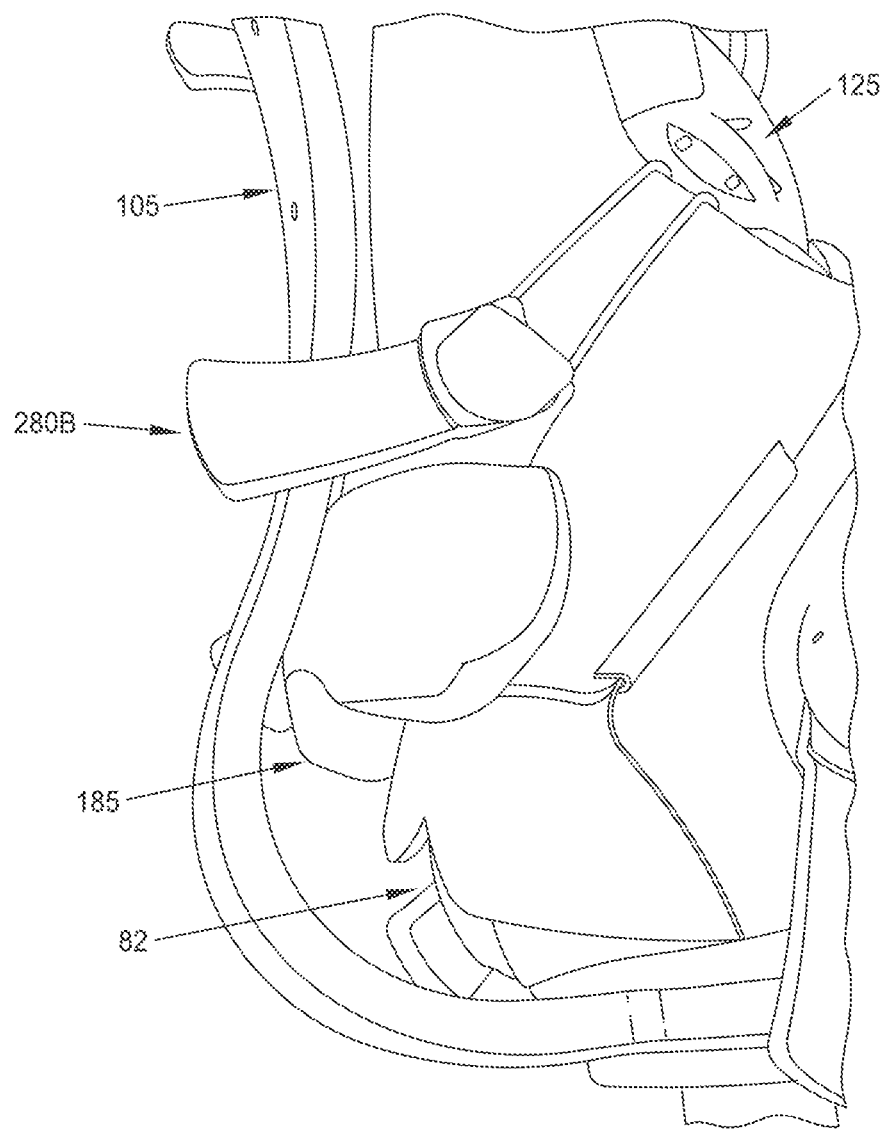
Figure 22:
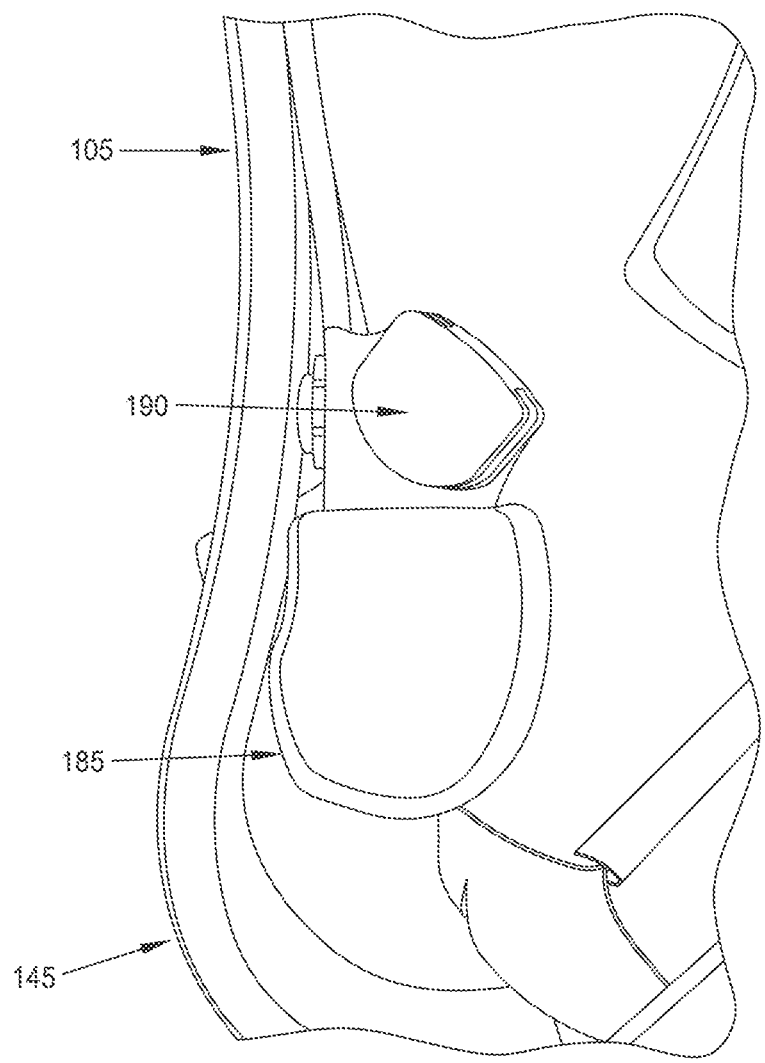
Figure 23:
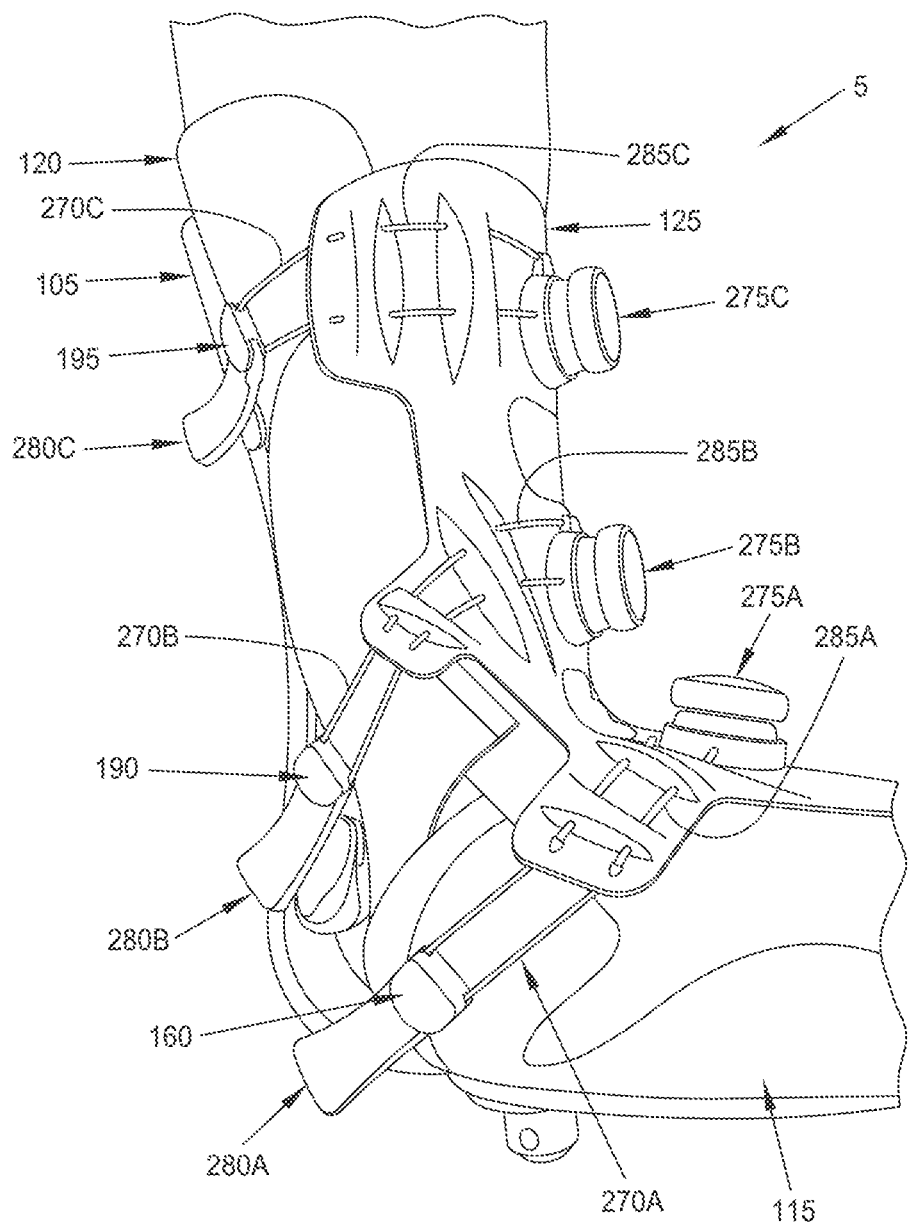

Plantar shell 115 (FIGS. 2-4, 10, 14-21, 23 and 24) is attached to plantar portion 140 of long, narrow spine 105. More particularly, plantar shell 115 comprises a base 153 which terminates short of the toes of the patient and which terminates short of the heel of the patient (FIGS. 2, 3 and 21). Plantar shell 115 further comprises flanges 155 and 156 (FIG. 15) which are separated by openings or cutouts 157. Flanges 155 and 156 serve to prevent the foot of the patient from rolling or pivoting relative to plantar shell 115 (and hence from rolling or pivoting relative to binding 35). Openings 157 between flanges 155 and 156 enable flanges 156 to flex when tension is applied to flanges 156 by cable assembly 130A (see below) so that flanges 156 closely conform to the foot of the patient, thereby improving the grip of binding 35 on the foot of the patient. Base 153 of plantar shell 115 preferably also comprises an outward relief 158 for reducing the pressure of the distal lower edge of base 153 of plantar shell 115 against the bottom of the foot of the patient (i.e., so that there is not a sharp edge that may cause iatrogenic damage to the foot of the patient).

In one preferred form of the invention, plantar shell 115 is formed out of a flexible plastic material (e.g., Nylon) which is sufficiently ductile to enable the plantar shell to conform to the anatomy of a patient while still being sufficiently firm to provide support to the anatomy of a patient.

Plantar shell 115 also comprises plantar cable mounts 160. Plantar cable mounts 160 are preferably formed on the aforementioned flanges 156. Plantar cable mounts 160 are intended to be aligned with lower band 40 of soft butterfly wrap 25, and to receive portions of cable assembly 130A, so that a gripping force can be applied about lower band 40 of soft butterfly wrap 25 when cable assembly 130A is tightened, as will hereinafter be discussed. In one preferred form of the invention, plantar cable mounts 160 may comprise "quick release" cable mounts of the sort adapted to receive and support portions of cable assembly 130A, as will hereinafter be discussed.

(iii) Calf Shell 120

Calf shell 120 (FIGS. 2, 3, 10 and 14-24) is attached to calf portion 150 of long, narrow spine 105. More particularly, calf shell 120 comprises a top portion 165 and a bottom portion 170. Significantly, and as will hereinafter be discussed in further detail, bottom portion 170 of calf shell 120 can flex relative to the remainder of calf shell 120 and terminates short of the heel of the patient.

Top portion 165 of calf shell 120 comprises flanges 175 (FIG. 19) which serve to prevent the anatomy of a patient from rolling or pivoting relative to calf shell 120 (and hence from rolling or pivoting relative to binding 35).

Bottom portion 170 of calf shell 120 projects toward the Achilles tendon of the patient, but stops short of the heel of the patient, as will hereinafter be discussed. Bottom portion 170 of calf shell 120 comprises flanges 180 which serve to prevent the anatomy of a patient from rolling or pivoting relative to calf shell 120 (and hence from rolling or pivoting relative to binding 35).

In one preferred form of the invention, bottom portion 170 of calf shell 120 further comprises a collar 185 set at the bottom end of bottom portion 170. Note that collar 185 also covers a portion of flanges 180. Collar 185 closely engages the anatomy of the patient in the region of the Achilles tendon. See FIGS. 17-19. More particularly, collar 185 is secured to bottom portion 170 of calf shell 120 and "nestles" around the anatomy of the patient just above the calcaneus, covering the Achilles tendon of the patient, whereby to closely engage the anatomy of the patient. In one form of the invention, collar 185 comprises a rubber member which covers and supports the anatomy of the patient, but is soft and compliant for comfort.

Note that flanges 175 (at the top portion 165 of calf shell 120) and flanges 180 (at the bottom portion 170 of calf shell 120) are separated from one another by openings or cutouts 187. Openings 187 between flanges 175 and flanges 180 enable flanges 175 to flex when tension is applied to flanges 175 by cable assembly 130C (see below) so that flanges 175 closely conform to the calf of the patient, thereby improving the grip of binding 35 on the leg of the patient; and openings 187 between flanges 175 and flanges 180 enable flanges 180 to flex when tension is applied to flanges 180 by cable assembly 130B (see below) so that flanges 180 closely conform to the region of the patient just proximal (i.e., superior) to the calcaneus, thereby improving the grip of binding 35 on the leg of the patient.

In one preferred form of the invention, calf shell 120 is formed out of a flexible plastic material (e.g., Nylon) which is sufficiently ductile to enable the calf shell to conform to the anatomy of a patient while still being sufficiently firm to provide support to the anatomy of a patient.

Bottom portion 170 of calf shell 120 comprises lower calf cable mounts 190, and top portion 165 of calf shell 120 comprises upper calf cable mounts 195. Top portion 165 of calf shell 120 is secured to calf portion 150 of long, narrow spine 105, and bottom portion 170 of calf shell 120 is free to flex in the region of lower cable mounts 190, i.e., bottom portion 170 of calf shell 120 is not secured to long, narrow spine 105, in order to allow bottom portion 170 of calf shell 120 to "float" in a cantilever fashion. Significantly, when tension is applied to flanges 180 by cable assembly 130B (see below), bottom portion 170 of calf shell 120 is flexed toward the anatomy of the patient, thereby improving the grip of binding 35 on the leg of the patient.

Lower cable mounts 190 are intended to be aligned with upper band 45 of soft butterfly wrap 25, and to receive portions of cable assembly 130B, so that a gripping force can be applied about upper band 45 of soft butterfly wrap 25 when cable assembly 130B is tightened, as will hereinafter be discussed. Note that inasmuch as bottom portion 170 of calf shell 120 is not secured to long, narrow spine 105 in order to allow bottom portion 170 to "float" in a cantilever fashion, bottom portion 170 of calf shell 120 is free to flex anteriorly when tension is applied to cable assembly 130B, whereby to enhance the engagement of collar 185 with the anatomy of the patient.

Upper calf cable mounts 195 are intended to be aligned with the lower- to mid-calf region of the patient, and to receive portions of cable assembly 130C, so that a gripping force can be applied about the lower- to mid-calf region of the patient when cable assembly 130C is tightened, as will hereinafter be discussed.

In one preferred form of the invention, lower calf cable mounts 190 comprise "quick release" cable mounts of the sort adapted to receive and support portions of cable assembly 130B, as will hereinafter be discussed, and upper calf cable mounts 195 comprise "quick release" cable mounts of the sort adapted to receive and support portions of cable assembly 130C, as will hereinafter be discussed.

Plantar shell 115 and calf shell 120 are spaced apart from one another in the region of the heel of the patient. In addition, curved portion 145 of long, narrow spine 105 is spaced away from the heel of the patient. Thus, binding 35 is open in the region of the heel of the patient, and does not cover the heel of the patient or otherwise engage the heel of the patient. This construction allows the surgical staff to visualize or measure the spacing of the heel of the patient from long, narrow spine 105.

(iv) Anterior Shell 125

Anterior shell 125 (FIGS. 2-4, 10, 14-16, 20, 21, 23 and 24) is connected to plantar shell 115 by cable assembly 130A, and anterior shell 125 is connected to calf shell 120 by cable assembly 130B and cable assembly 130C. Tensioning of cable assemblies 130A, 130B and 130C causes anterior shell 125 of binding 35 to move towards plantar shell 115 and calf shell 120, and tensioning of cable assembly 130B causes bottom portion 170 of calf shell 120 to flex anteriorly towards the Achilles tendon of the patient, so that binding 35 securely grips the anatomy of the patient.

In one preferred form of the invention, anterior shell 125 comprises a first section 200, a second section 205 and a third section 210. First section 200 is connected to second section 205 by a pair of webs 215, and second section 205 is connected to third section 210 by a pair of webs 220.

Referring to FIG. 4, first section 200 of anterior shell 125 comprises flanges 235 and cable guides 240. First section 200, flanges 235 and cable guides 240 are intended to be aligned with lower band 40 of soft butterfly wrap 25, and to receive portions of cable assembly 130A, so that a gripping force can be applied about lower band 40 of soft butterfly wrap 25 when cable assembly 130A is tightened, as will hereinafter be discussed.

Second section 205 of anterior shell 125 comprises flanges 245 and cable guides 250. Second section 205, flanges 245 and cable guides 250 are intended to be aligned with upper band 45 of soft butterfly wrap 25, and to receive portions of cable assembly 130B, so that a gripping force can be applied about upper band 45 of soft butterfly wrap 25 when cable assembly 130B is tightened, as will hereinafter be discussed.

Third section 210 of anterior shell 125 comprises flanges 255 and cable guides 260. Third section 210, flanges 255 and cable guides 260 are intended to be aligned with the lower- to mid-calf region of the patient, and to receive portions of cable assembly 130C, so that a gripping force can be applied about the lower- to mid-calf region of the patient when cable assembly 130C is tightened, as will hereinafter be discussed.

Openings or cutouts 300 (FIG. 4) are provided between flanges 235 and 245, and openings or cutouts 305 are provided between flanges 245 and 255, and an opening or cutout 310 is provided between first section 200 and second section 205, and an opening or cutout 315 is provided between second section 205 and third section 210, in order to provide flexibility to anterior shell 125 which enables anterior shell 125 to conform to the foot and lower leg of the patient as cable assemblies 130A, 130B and 130C are tightened. A flange 267, extending distally from first section 200 of anterior shell 125 (FIG. 4), distributes load onto the dorsal portion of the foot to prevent pressure points. An opening or cutout 320 provides flexibility to flange 267 so that excess pressure is not applied to the dorsal portion of the foot.

In one preferred form of the invention, anterior shell 125 is formed out of a flexible plastic material (e.g., Nylon) which is sufficiently ductile to enable the anterior shell to conform to the anatomy of a patient while still being sufficiently firm to provide support to the anatomy of a patient.

Figure 24:
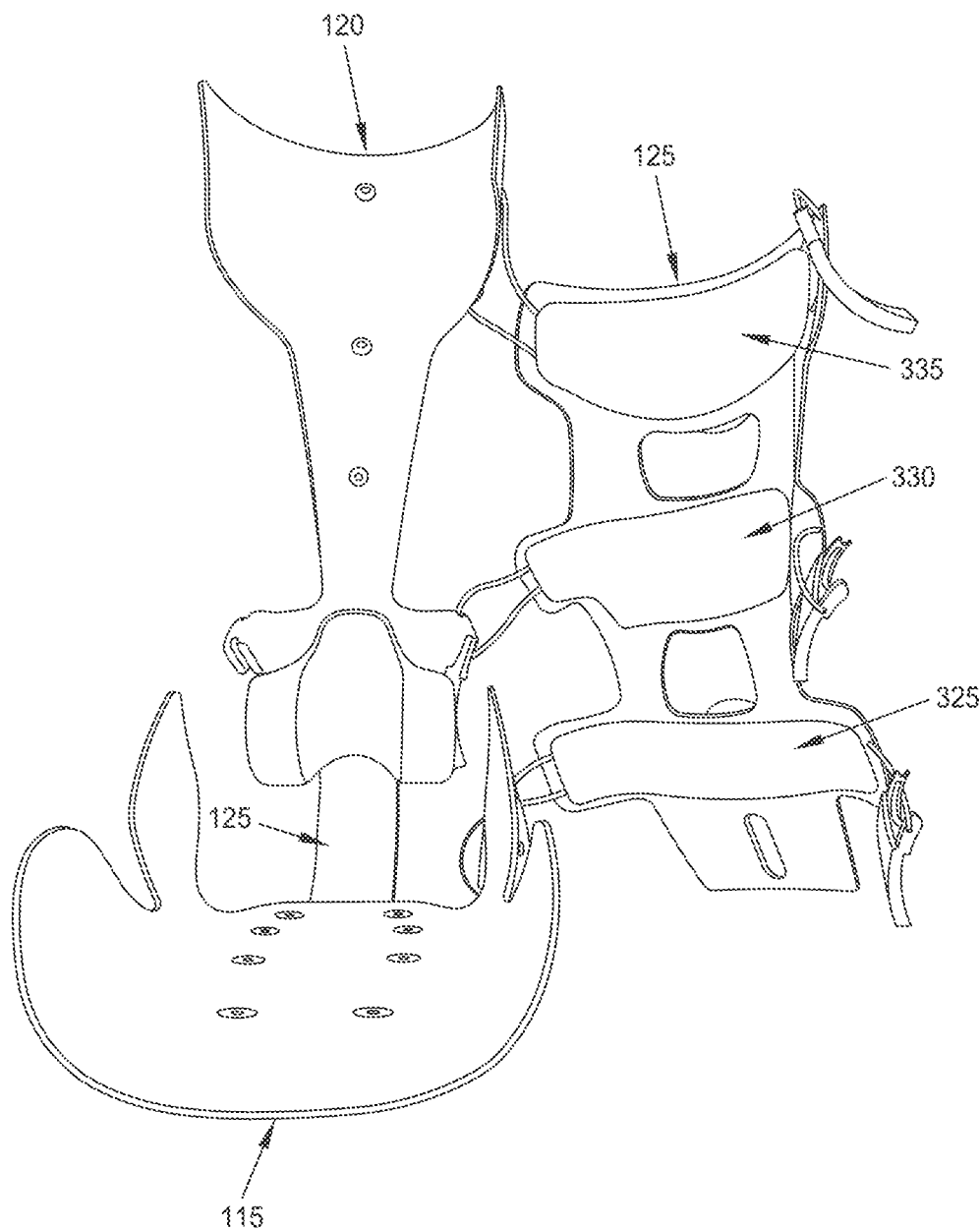
Figure 25:
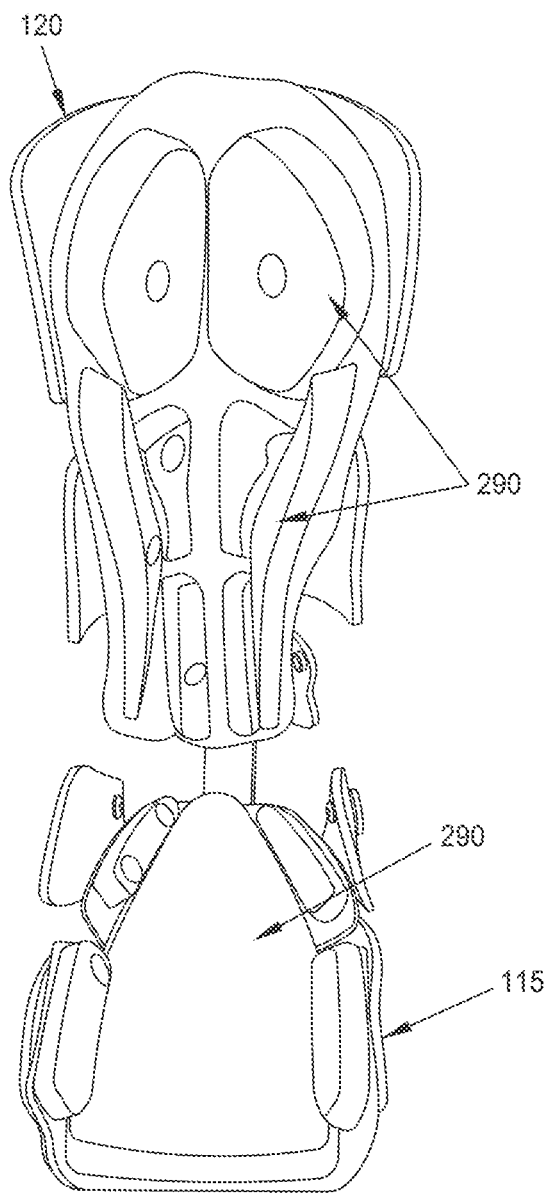
Figure 26:
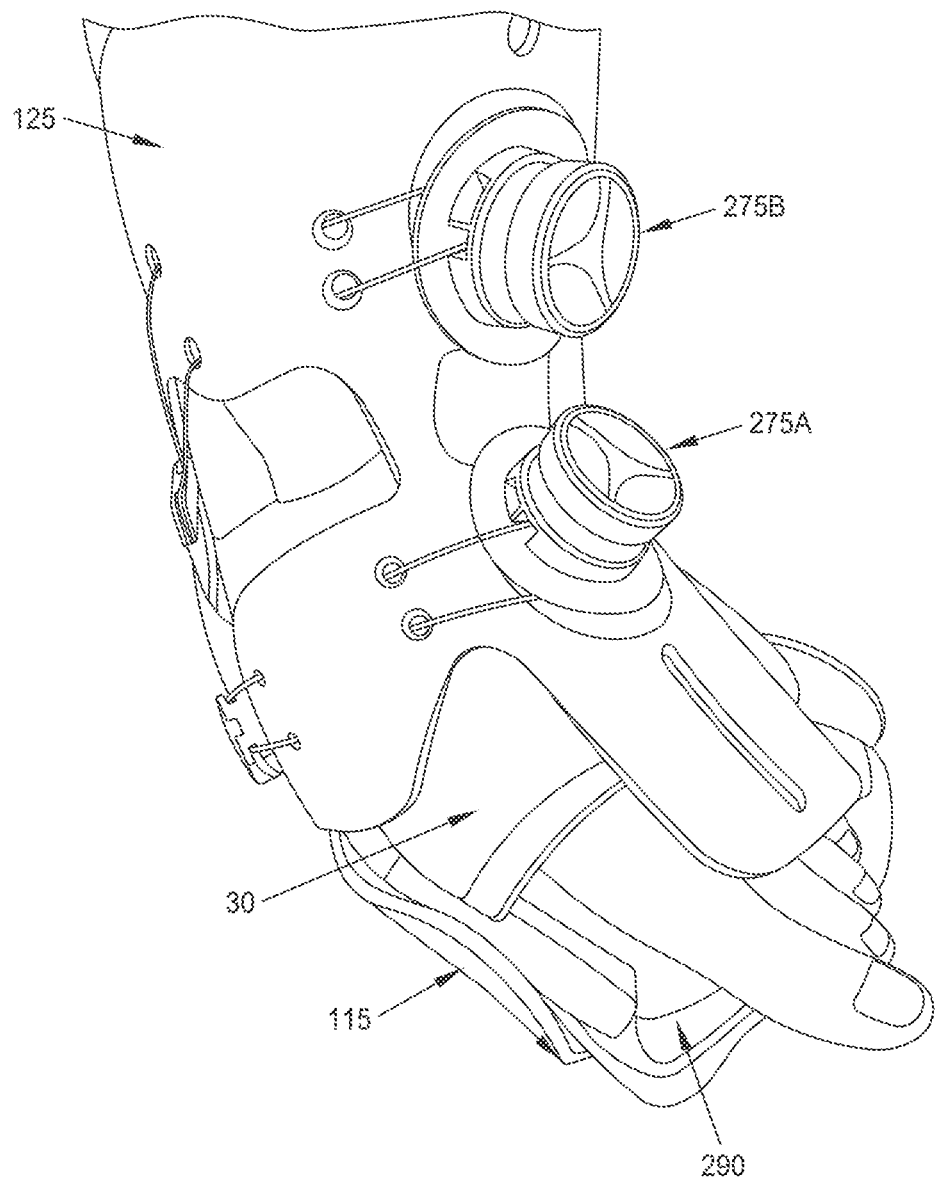
Figure 27:
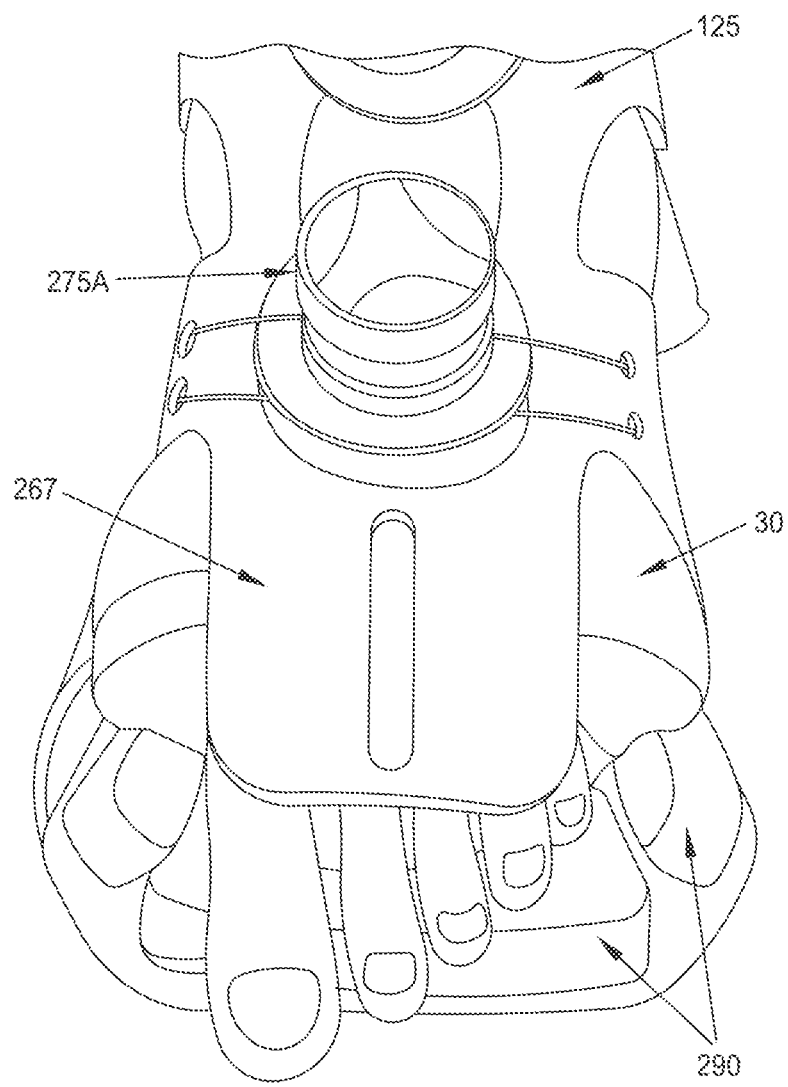
Figure 28:
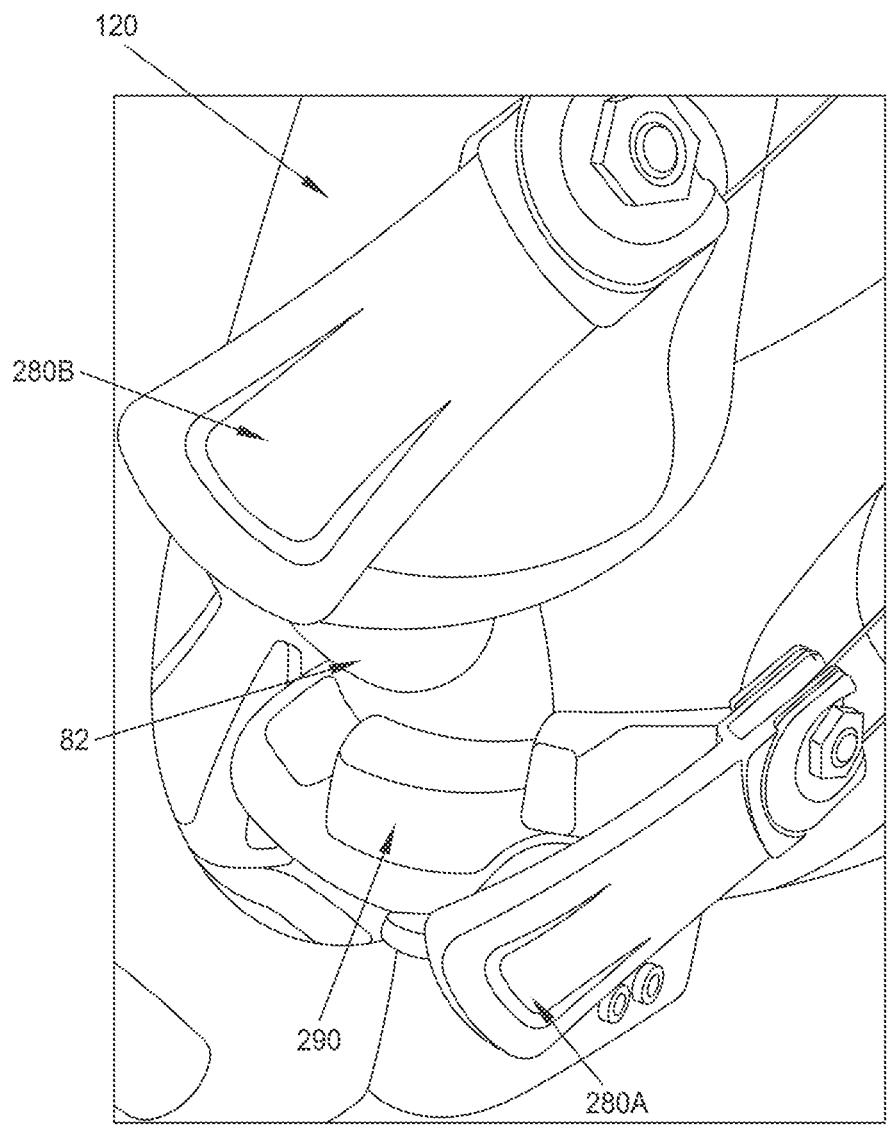
Figure 29:
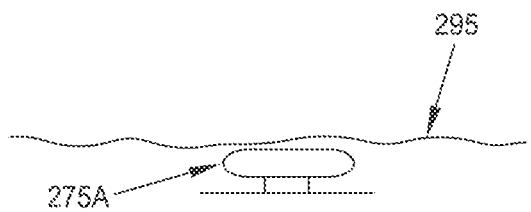
Figure 30:
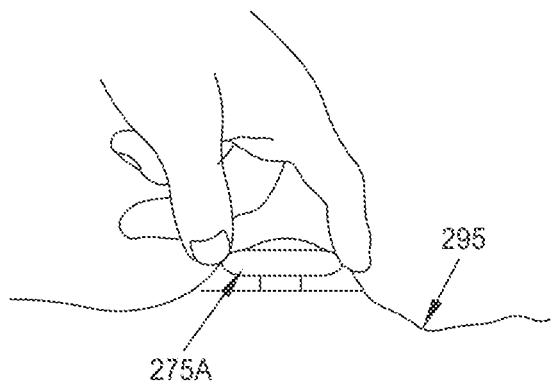
Figure 31:
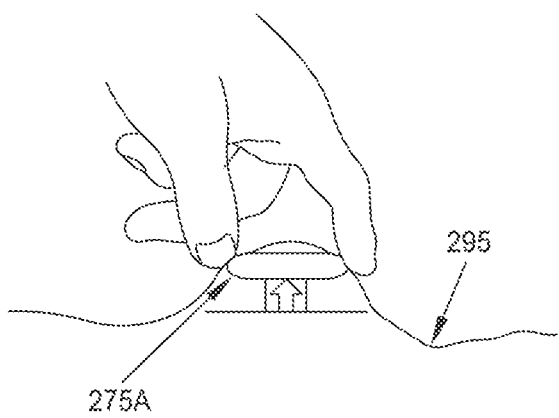
Figure 32:
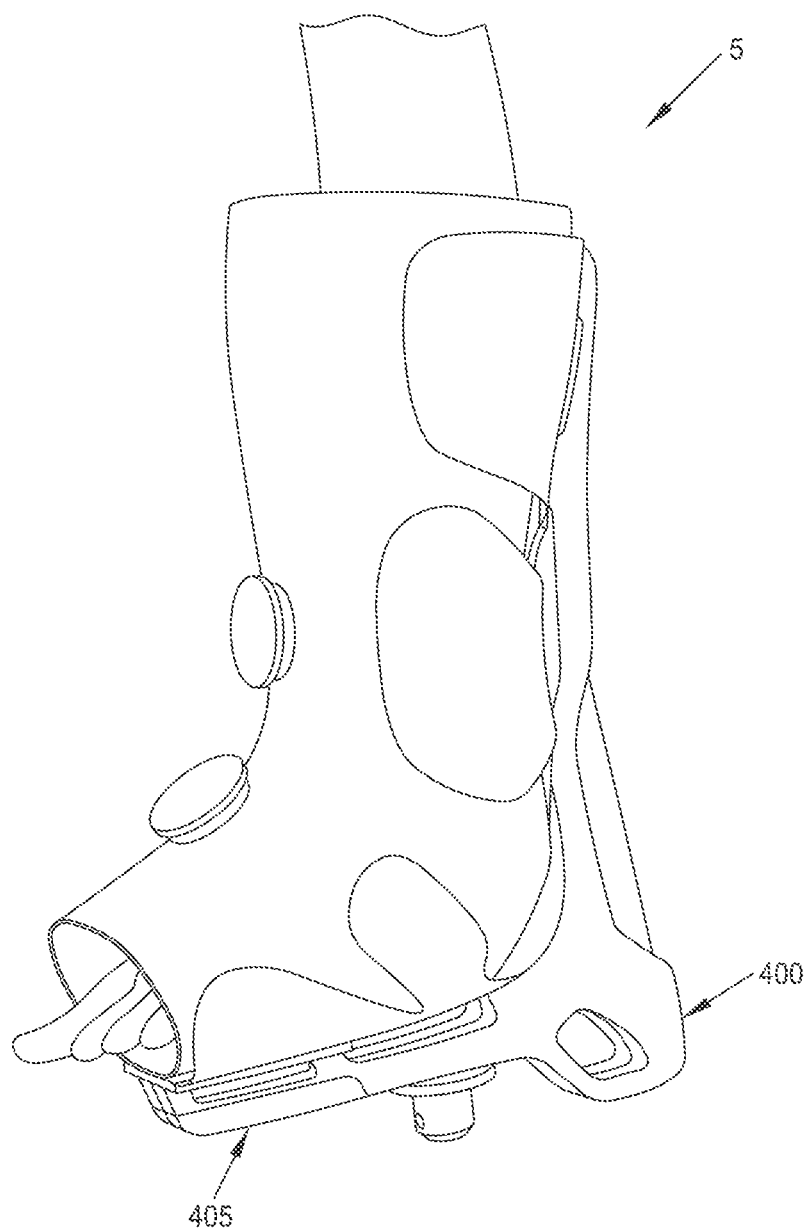

If desired, and looking now at FIG. 24, anterior shell 125 may comprise a rubber cushion 325 on the inside surface of first section 200 of anterior shell 125, and a rubber cushion 330 on the inside surface of second section 205 of anterior shell 125, and a rubber cushion 335 on the inside surface of third section 210 of anterior shell 120. Rubber cushions 325, 330, 335 may comprise a rubber (or foam rubber) material of a durometer which is softer than anterior shell 125 but firmer than soft liner 30. Thus, in this construction, soft liner 30, rubber cushions 325, 330, 335 and anterior shell 125 have increasing durometers, which assists in distributing loads from anterior shell 125 onto the foot of the patient, thereby reducing high pressure locations on the foot.

(v) Cable Assemblies 130A, 130B And 130C

Cable assembly 130A connects anterior shell 125 to plantar shell 115, and cable assemblies 130B and 130C connect anterior shell 125 to calf shell 120. Tensioning of cable assemblies 130A, 130B and 130C causes anterior shell 125 of binding 35 to move towards plantar shell 115 and calf shell 120 (FIG. 10), and tensioning of cable assembly 130B causes bottom portion 170 of calf shell 120 to flex anteriorly towards the Achilles tendon of the patient (FIG. 10), so that binding 35 securely grips the anatomy of the patient.

Cable assembly 130A comprises a cable 270A, a rotary tightening mechanism 275A disposed intermediate cable 270A for tensioning cable 270A, and a pair of pull tabs 280A disposed at opposing ends of cable 270A. If desired, cable guards 285A may be mounted to first section 200 of anterior shell 125 to guide cable 270A as it passes along first section 200 of anterior shell 125. Rotary tightening mechanism 275A is mounted to first section 200 of anterior shell 125, cable 270A is passed through cable guides 240 (and cable guards 285A if they are provided), and pull tabs 280A are used to facilitate mounting and dismounting of cable 270A to plantar cable mounts 160.

Figure 10:
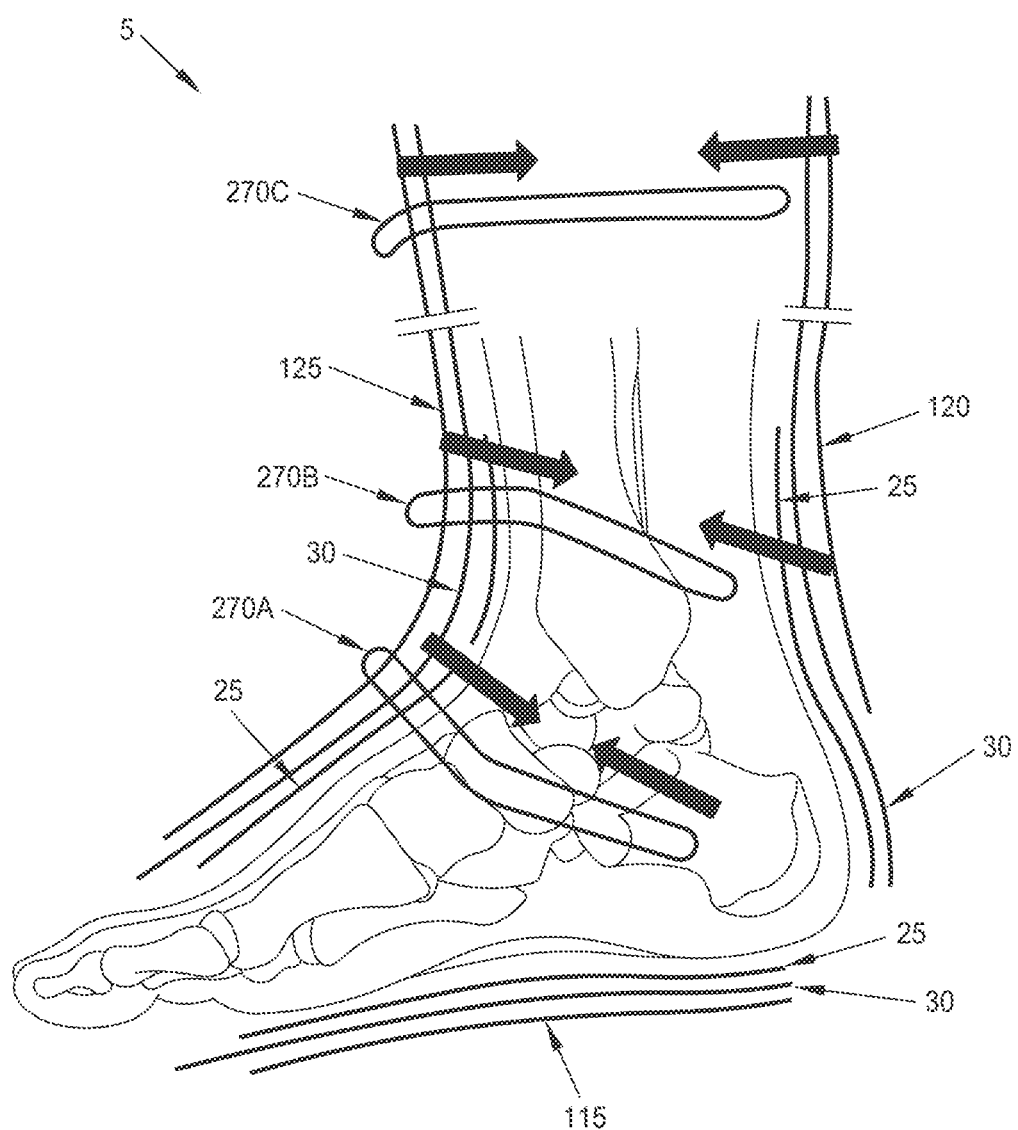
FIG. 10 is a schematic view showing how the novel anatomical gripping system of the present invention applies forces to the foot and lower leg of a patient.
Figure 11:
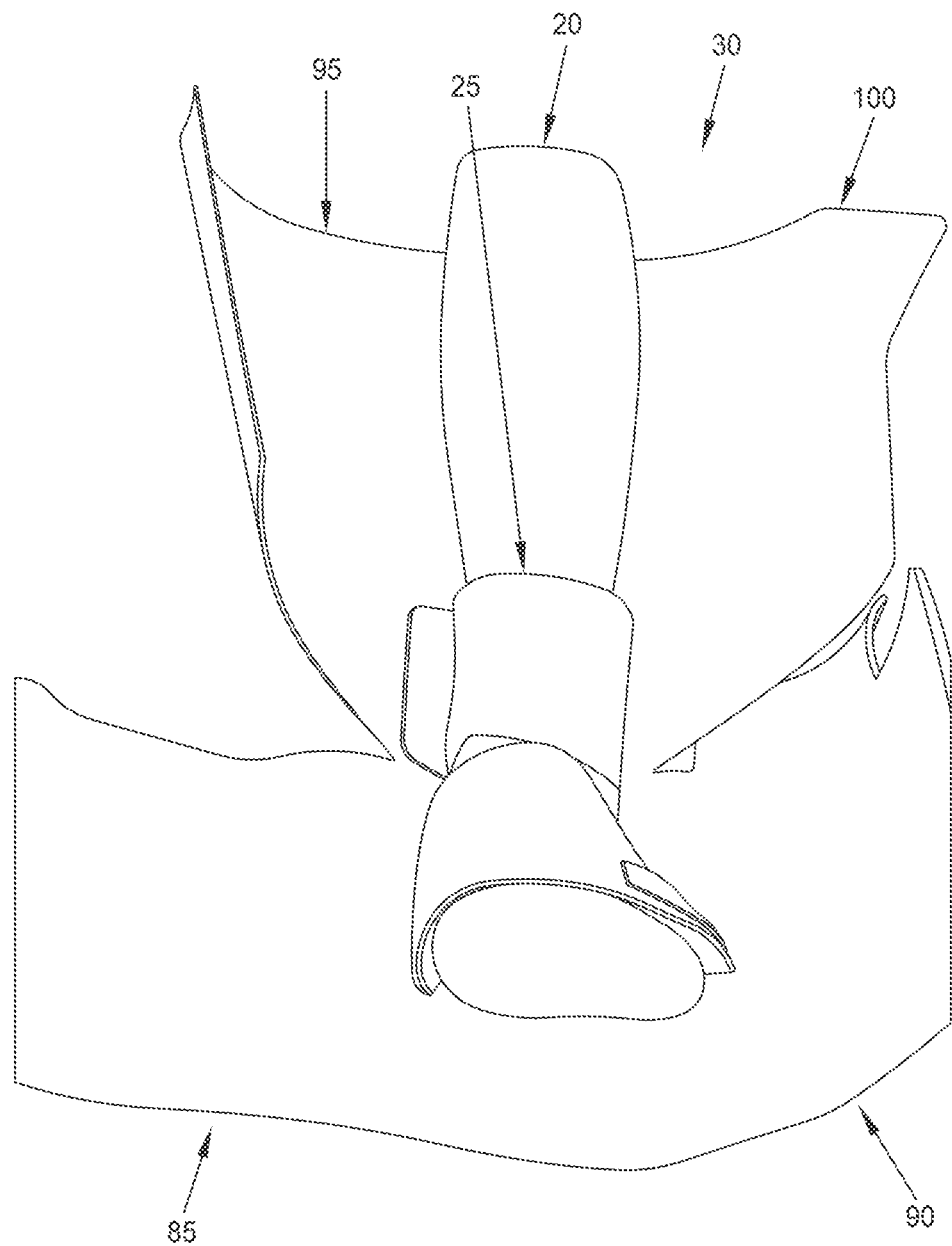
FIGS. 11, 12, 12A, 12B and 13 are schematic views showing further details of the soft liner of the novel anatomical gripping system of the present invention.
Figure 12:
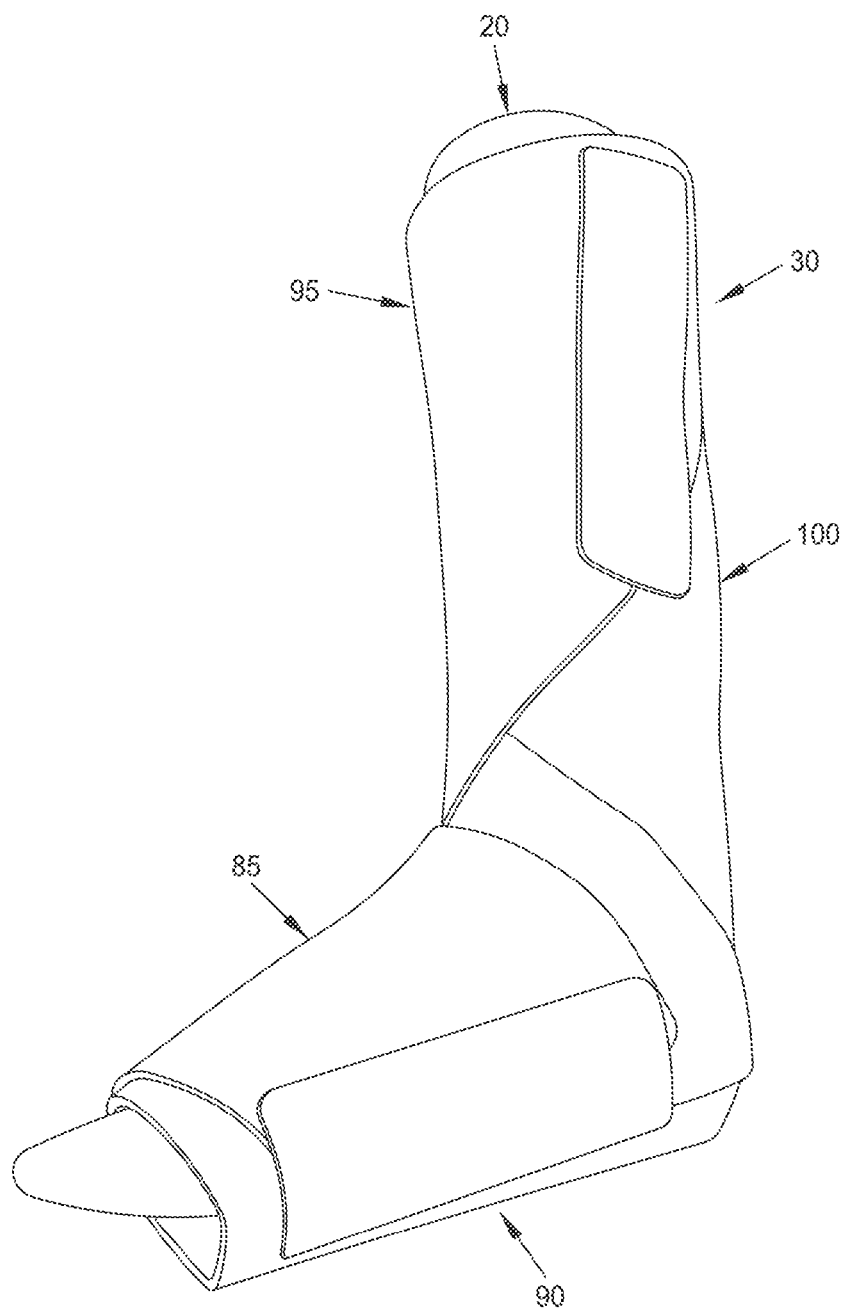
Figure 12A:
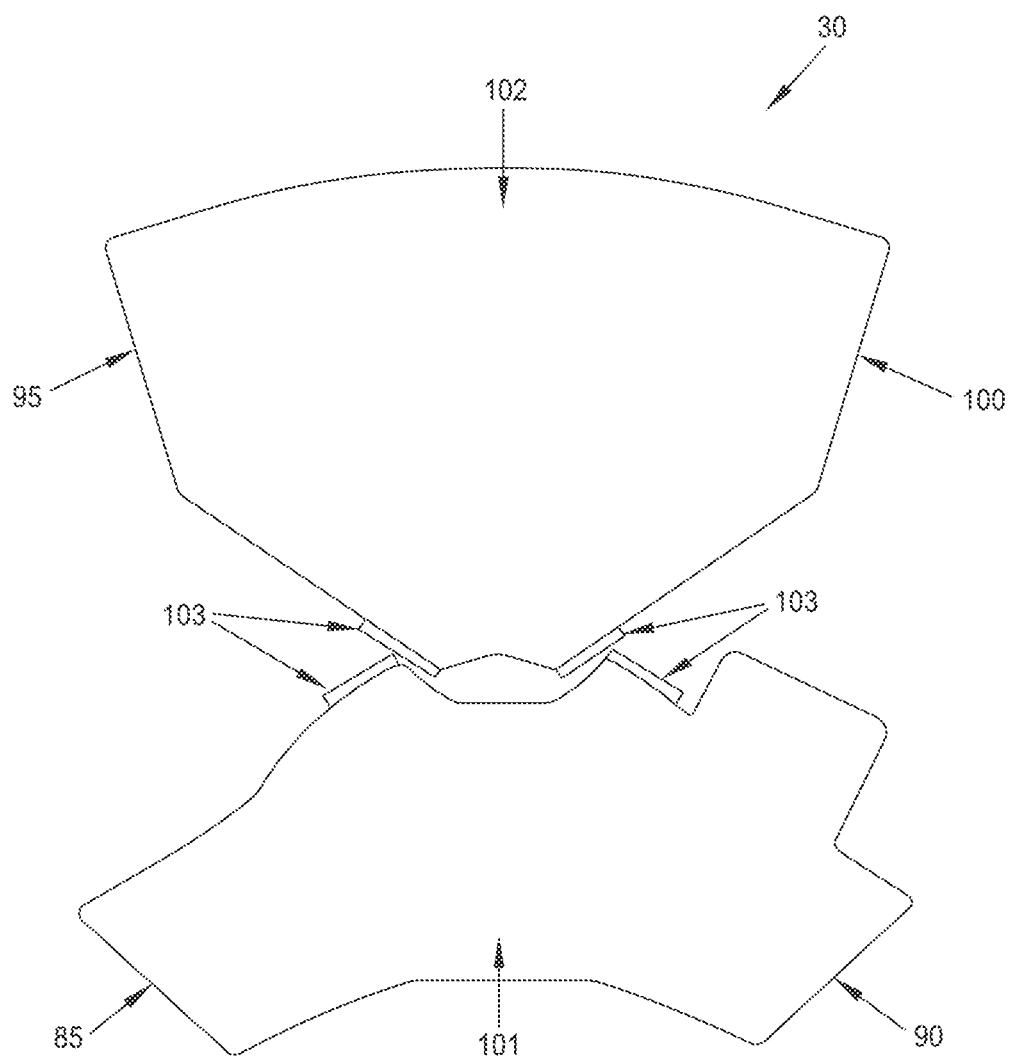
Figure 12B:
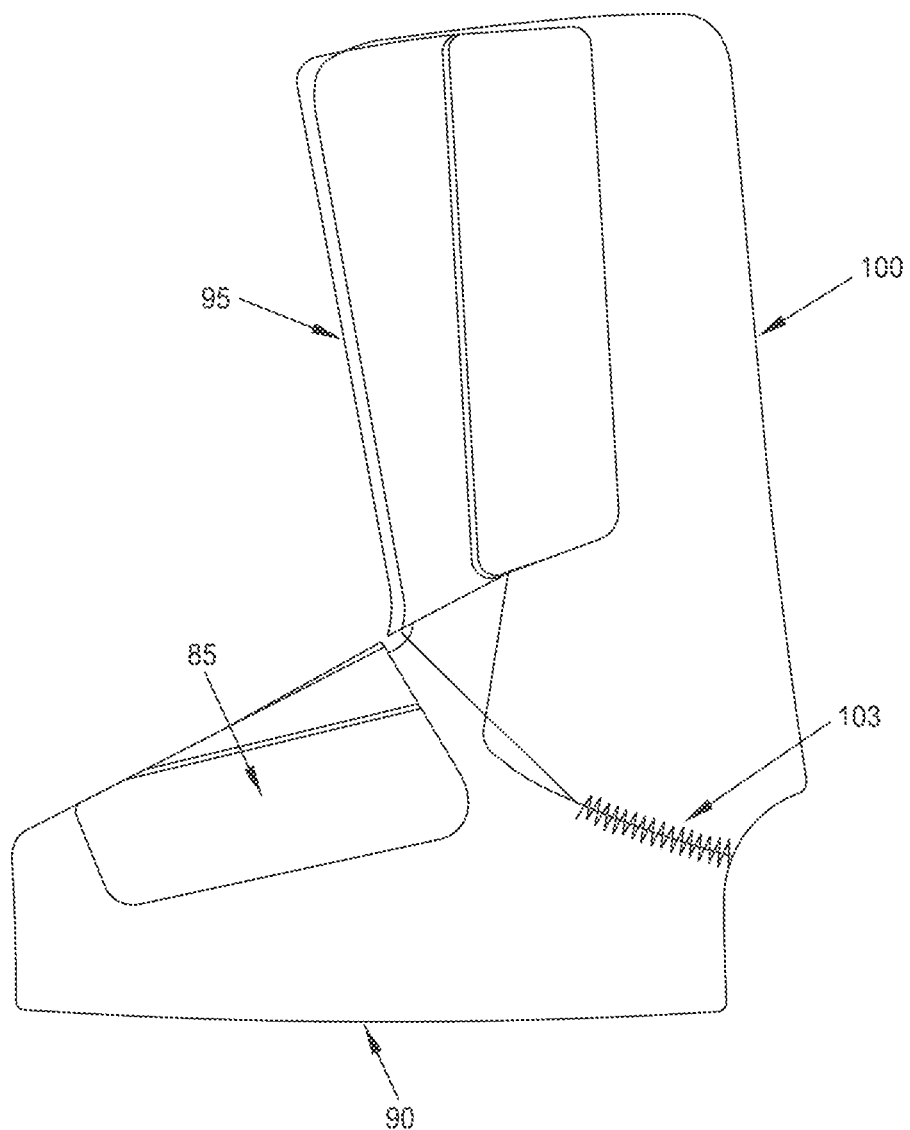
Figure 13:
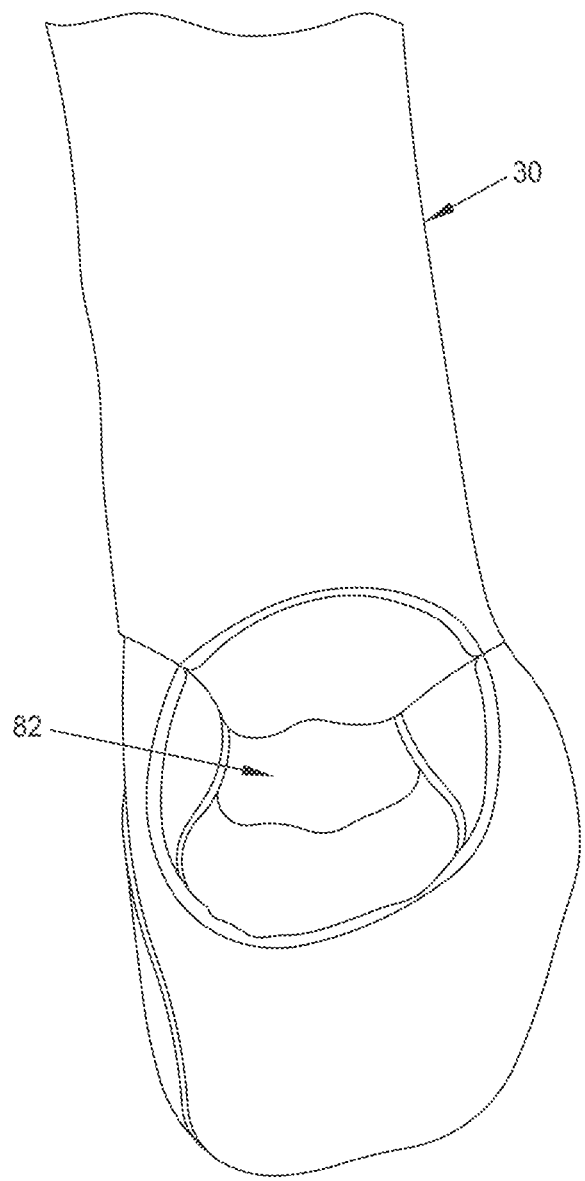
Figure 13A:
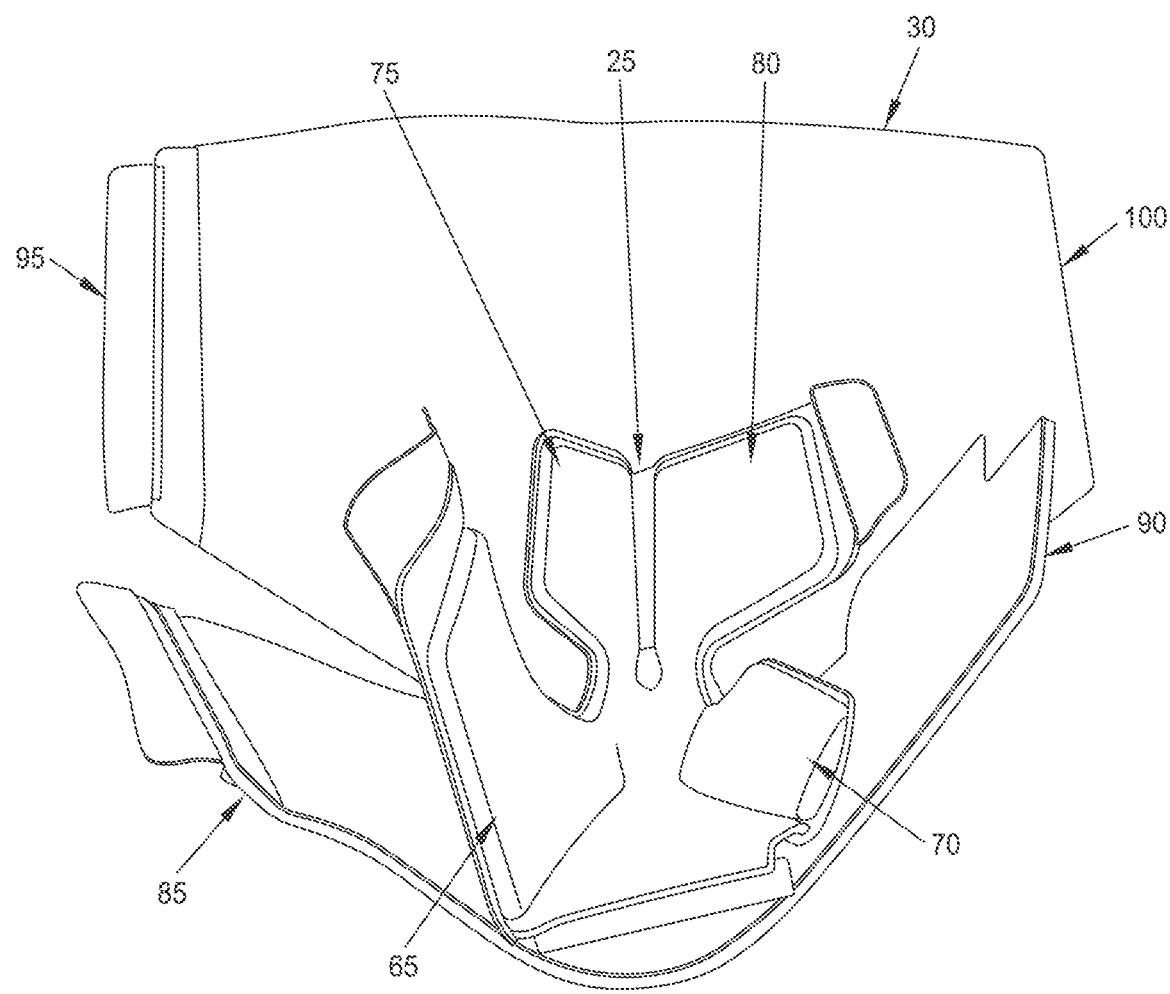
FIG. 13A is a schematic view showing further details of the soft butterfly wrap and the novel soft liner of the anatomical gripping system of the present invention.
Figure 14:
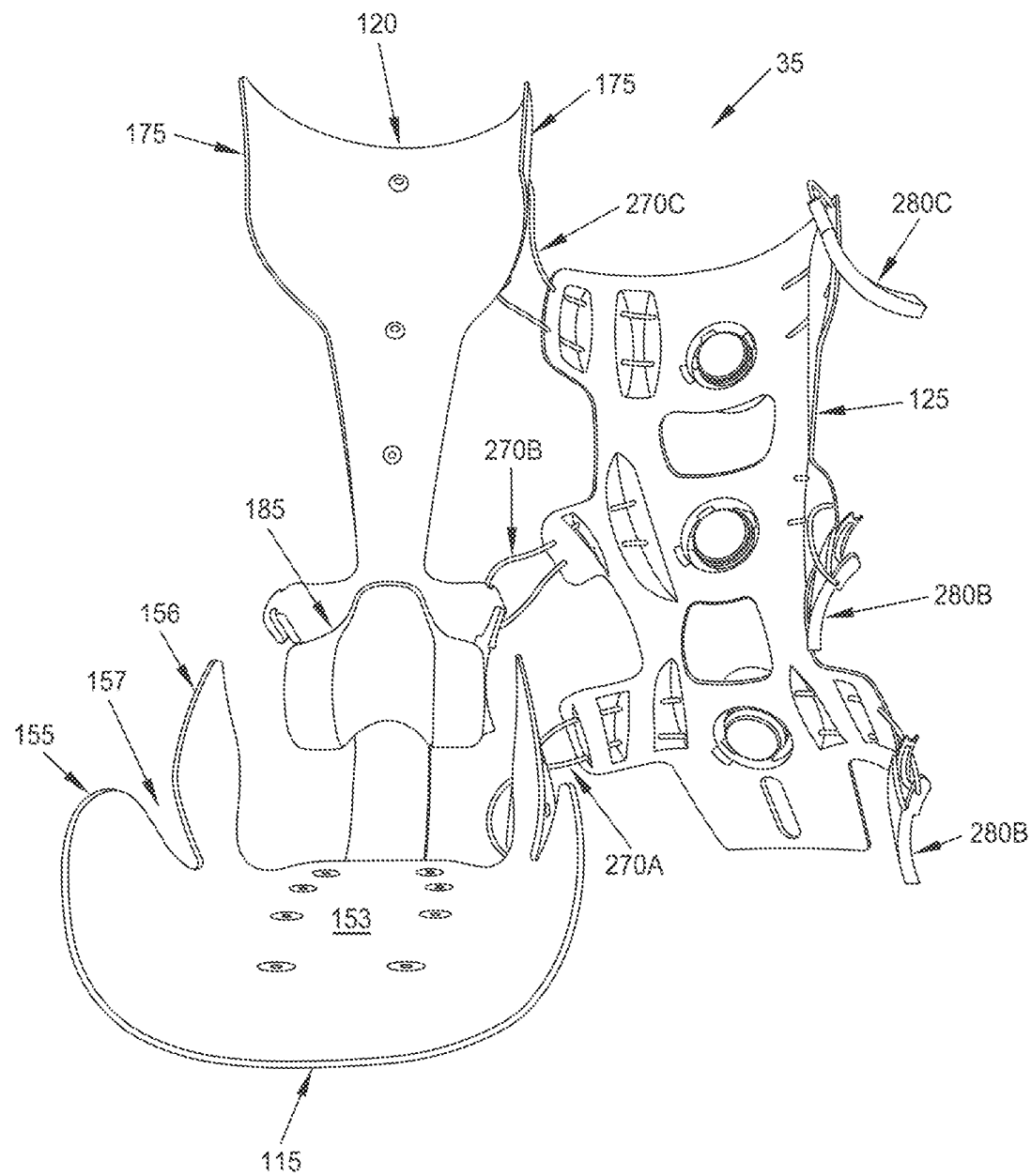
FIGS. 14-34 are schematic views showing further details of the binding of the novel anatomical gripping system of the present invention.
Figure 15:
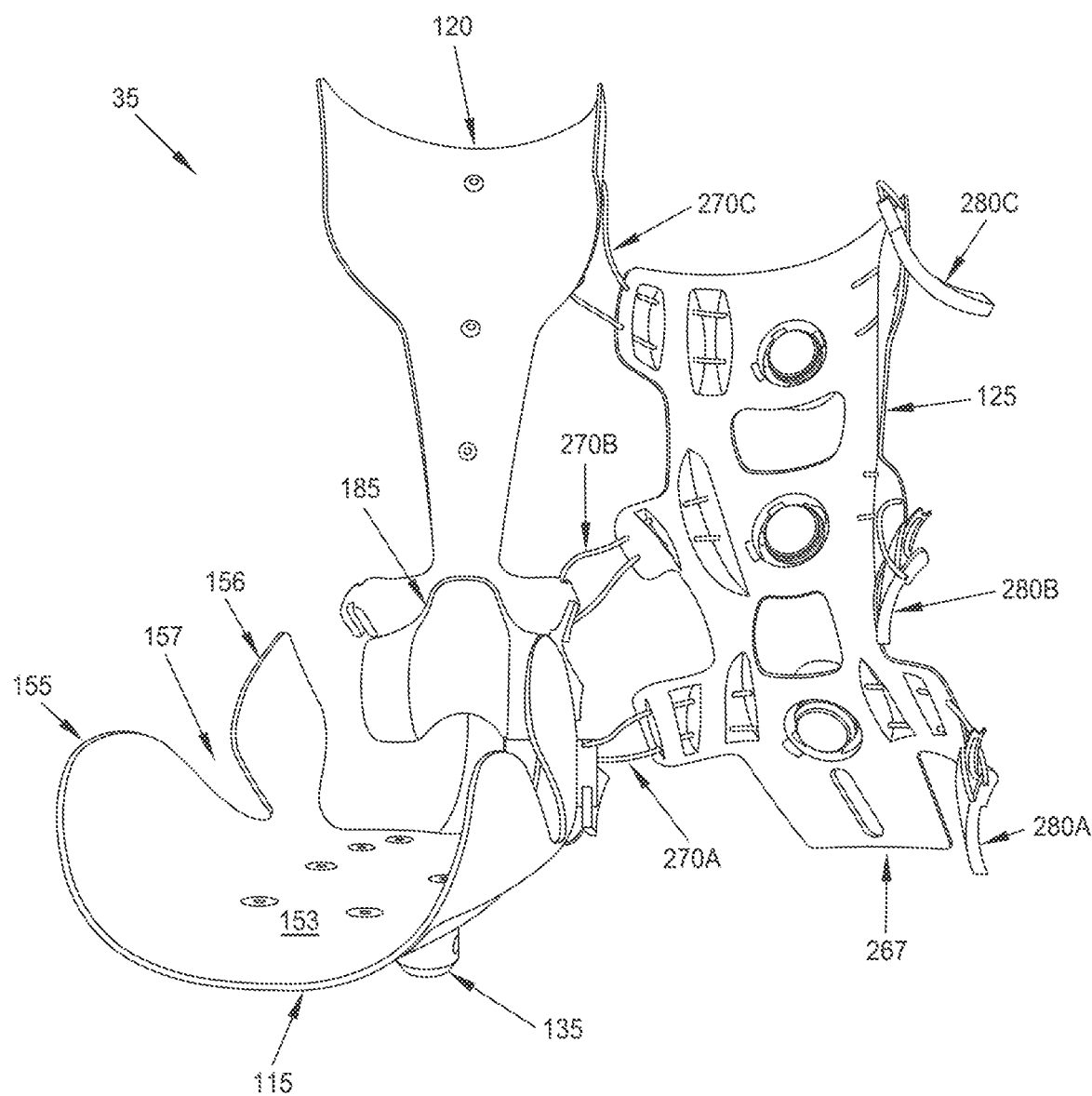
Figure 16:
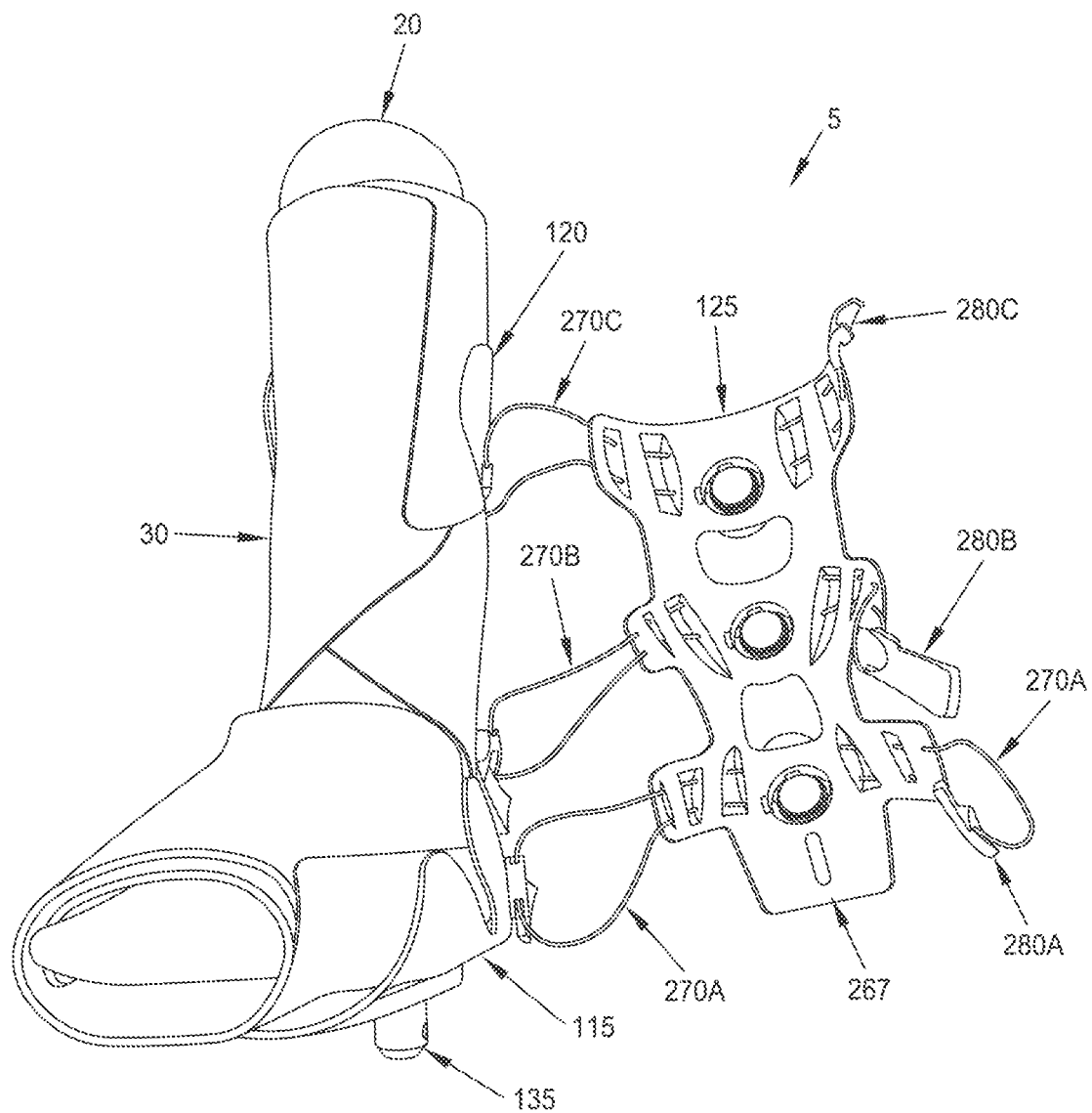
Figure 17:
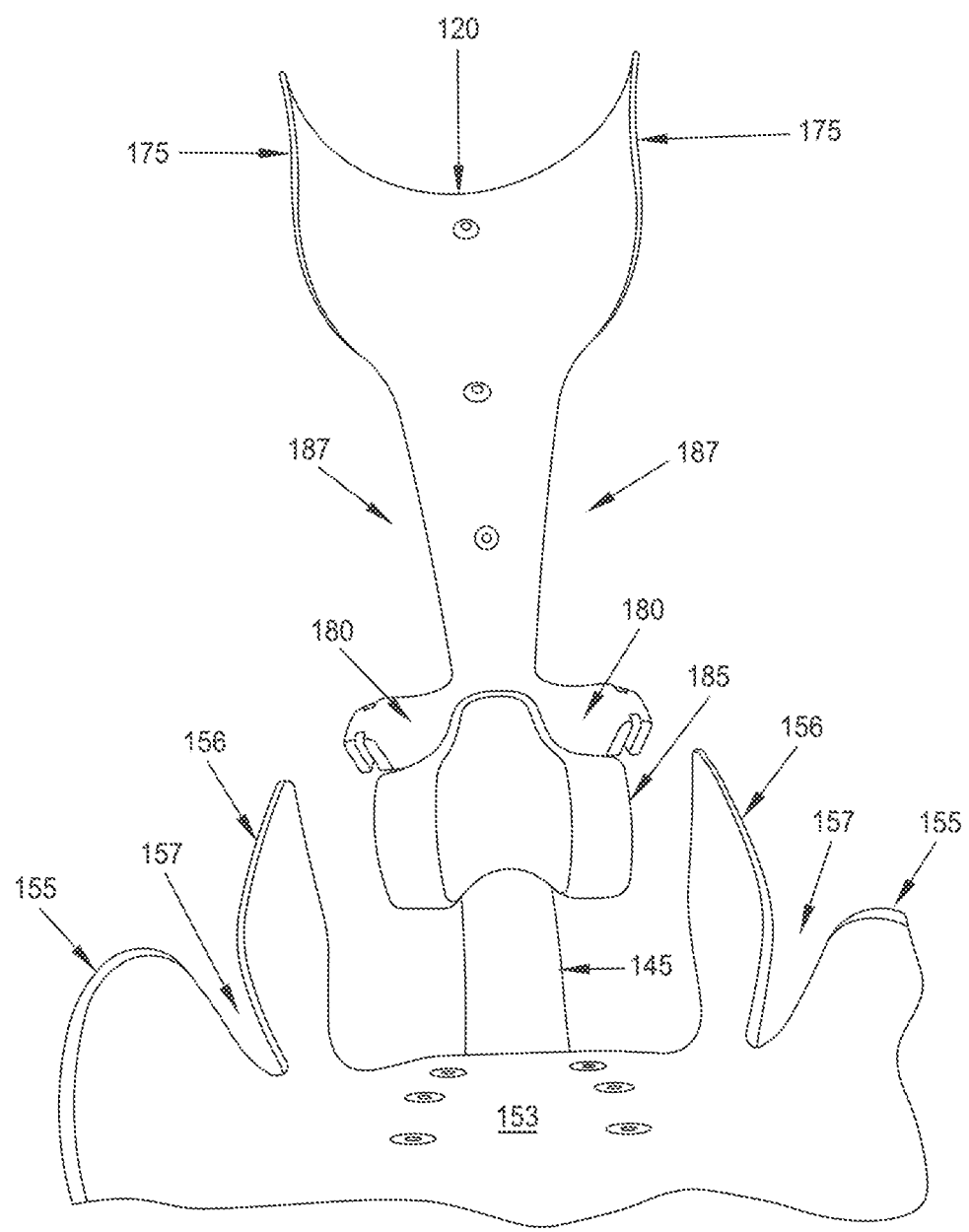
Figure 18:
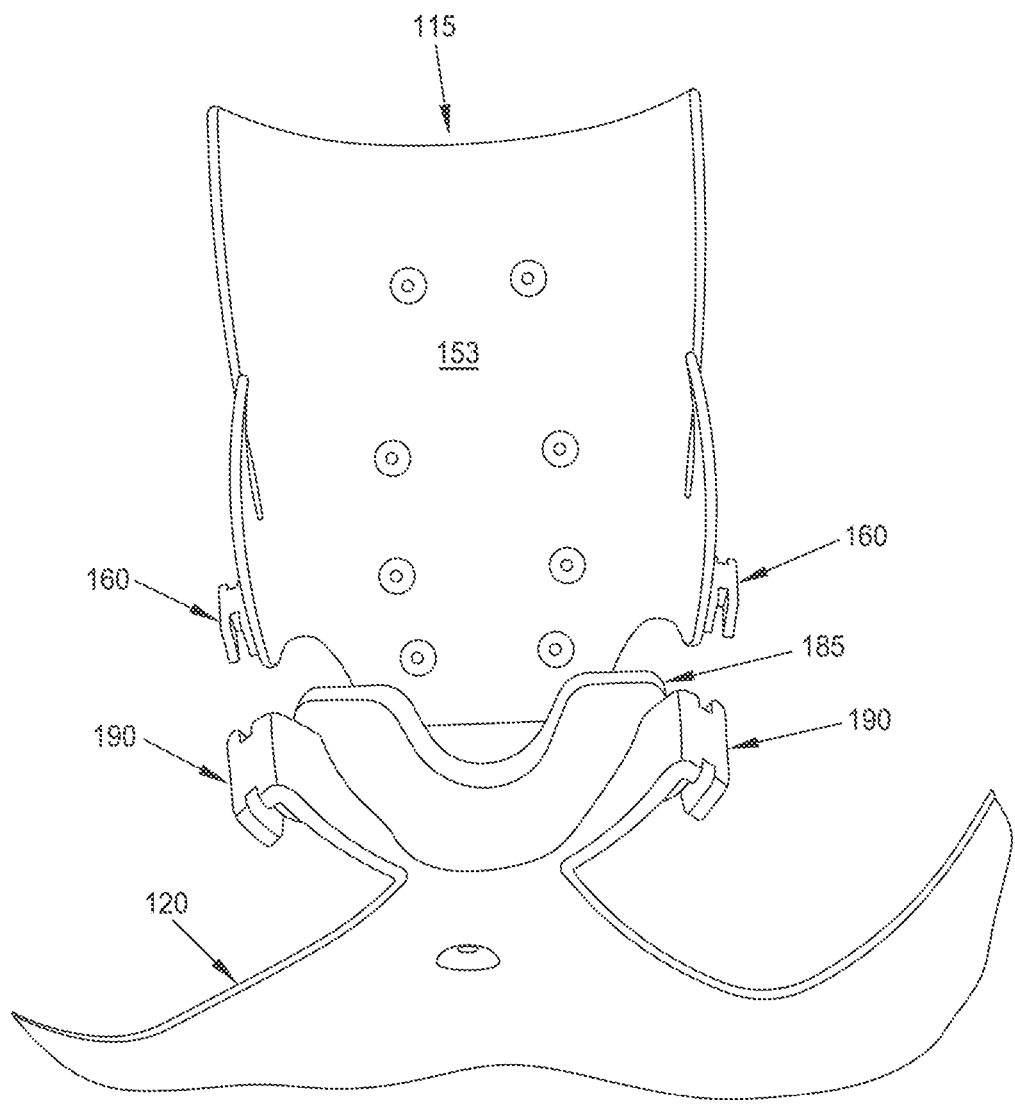
Figure 19:
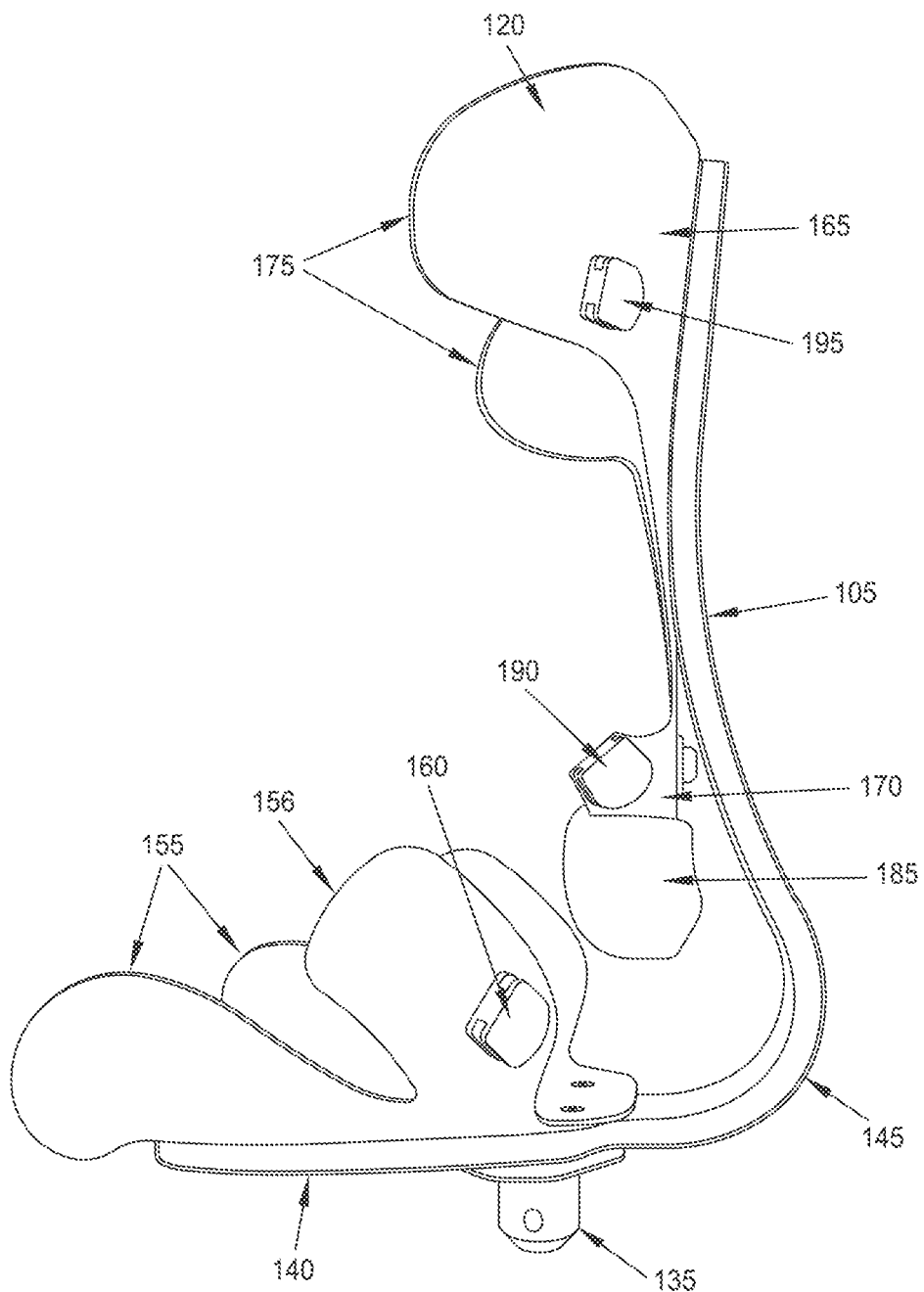
Figure 20:
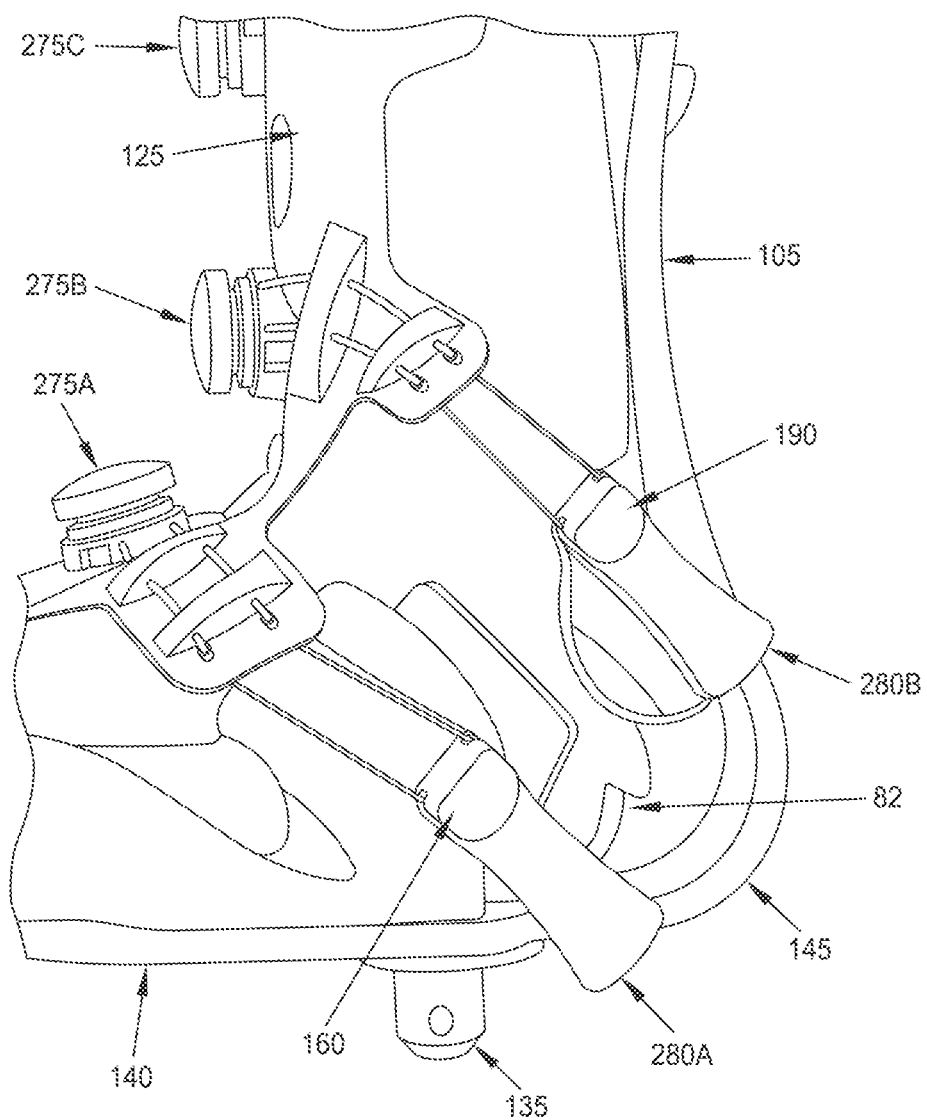

On account of the foregoing construction, when cable 270A is mounted on plantar cable mounts 160 and rotary tightening mechanism 275A is thereafter turned, cable 270A can be shortened (i.e., tightened) so as to cause binding 35 to apply a gripping force about lower band 40 of soft butterfly wrap 25, i.e., around the mid-foot and forefoot of the patient, thereby providing substantial gripping of the patient's anatomy (FIG. 10).

Cable assembly 130B comprises a cable 270B, a rotary tightening mechanism 275B disposed intermediate cable 270B for tensioning cable 270B, and a pair of pull tabs 280B disposed at opposing ends of cable 270B. If desired, cable guards 285B may be mounted to second section 205 of anterior shell 125 to guide cable 270B as it passes along second section 205 of anterior shell 125. Rotary tightening mechanism 275B is mounted to second section 205 of anterior shell 125, cable 270B is passed through cable guides 250 (and cable guards 285B if they are provided), and pull tabs 280B are used to facilitate mounting and dismounting of cable 270B to lower calf cable mounts 190.

On account of the foregoing construction, when cable 270B is mounted on lower calf cable mounts 190 and rotary tightening mechanism 275B is thereafter turned, cable 270B can be shortened (i.e., tightened) so as to cause binding 35 to apply a gripping force about upper band 45 of soft butterfly wrap 25, i.e., superior (i.e., proximal) to the malleoli bones, thereby providing substantial gripping of the patient's anatomy (FIG. 10).

Cable assembly 130C comprises a cable 270C, a rotary tightening mechanism 275C disposed intermediate cable 270C for tensioning cable 270C, and a pair of pull tabs 280C disposed at opposing ends of cable 270C. If desired, cable guards 285C may be mounted to third section 210 of anterior shell 125 to guide cable 270C as it passes along third section 210 of anterior shell 125. Rotary tightening mechanism 275C is mounted to third section 210 of anterior shell 125, cable 270C is passed through cable guides 260 (and cable guards 285C if they are provided), and pull tabs 280C are used to facilitate mounting and dismounting of cable 270C to upper calf cable mounts 195.

On account of the foregoing construction, when cable 270C is mounted on upper calf cable mounts 195 and rotary tightening mechanism 275C is thereafter turned, cable 270C can be shortened (i.e., tightened) so as to cause binding 35 to apply a gripping force about the lower- to mid-calf region of the patient, thereby providing substantial gripping of the patient's anatomy (FIG. 10).

Rotary tightening mechanisms 275A, 275B and 275C are provided for selectively tensioning cables 270A, 270B and 270C, respectively. If desired, rotary tightening mechanisms 275A, 275B and 275C may comprise a "quick release" button. In one preferred form of the invention, rotary tightening mechanisms 275A, 275B and 275C comprise rotary tightening mechanisms of the sort provided by Boa Technology, Inc. of Colorado, USA. Boa rotary tightening mechanisms are generally preferred inasmuch as the Boa rotary tightening mechanisms provide symmetrical tightening which is applied equally to both sides of binding 35 when the rotary tightening mechanisms are tightened. Rotary tightening mechanisms 275A, 275B and 275C may comprise Boa's "high power" model which has a higher gear ratio for increased tensioning of the cables. Alternatively, rotary tightening mechanism 275C may comprise a "low power" Boa model and rotary tightening mechanisms 275A and 275B may comprise a "high power" Boa model.

In one preferred form of the invention, cables 270A, 270B and 270C pass through cable guards 285A, 285B and 285C, respectively, which themselves pass through cable guides 240, 250 and 260, respectively, in anterior shell 125. However, it should be appreciated that, if desired, cable guards 285A, 285B and 285C may be omitted; in such case, cables 270A, 270B and 270C may be passed directly through cable guides 240, 250 and 260, respectively, in anterior shell 125.

D. The Unique Manner in which Binding 35 Grips the Anatomy of the Patient

As discussed above, cable assemblies 130A, 130B and 130C function as follows:

(i) tensioning of cable 270A of cable assembly 130A draws anterior shell 125 onto the dorsal portion of the foot of the patient, whereby to apply a gripping force to the mid-foot and forefoot of the patient (FIG. 10), with flanges 155 of plantar shell 115 and flanges 156 of plantar shell 115 closely conforming to the mid-foot of the patient;

(ii) tensioning of cable 270B of cable assembly 130B draws anterior shell 125 towards the front of the lower leg of the patient and draws bottom portion 170 of calf shell 120 in against the anatomy of the patient superior to the calcaneus, whereby to apply a gripping force to the lower leg of the patient superior to the malleoli bones (and superior to the calcaneus) (FIG. 10), with flanges 180 of calf shell 120 and flanges 245 of anterior shell 125 closely conforming to the lower leg of the patient proximal (i.e., superior) to the malleoli bones, and proximal (i.e., superior) to the calcaneus; and (iii) tensioning of cable 270C of cable assembly 130C draws anterior shell 125 against the lower leg of the patient so as to apply a gripping force to the patient about the lower- to mid-calf region of the patient (FIG. 10), with flanges 175 of calf shell 120 and flanges 255 of anterior shell 125 closely conforming to the lower- to mid-calf region of the patient.

The combination of the three aforementioned gripping actions provides for unique gripping of the anatomy of the patient.

Significantly, cable assembly 130B causes binding 35 to clamp the anatomy just proximal (i.e., superior) to the malleoli (FIG. 10). More particularly, when rotary tightening mechanism 275B is turned and cable 270B is tightened, anterior shell 125 and calf shell 120 tighten down on the anatomy just proximal (i.e., superior) to the malleoli, which together present a large, protruding diameter of hard bony anatomy. As a result, when a distally-directed distraction force is thereafter applied to binding 35, the portions of binding 35 gripping the anatomy just proximal (i.e., superior) to the malleoli are unable to slip past the malleoli, due to the tight engagement of the binding on the anatomy just proximal (i.e., superior) to the malleoli and due to the enlarged body diameter of the malleoli.

It should also be appreciated that when rotary tightening mechanism 275B is turned and cable 270B is shortened (i.e., tightened), the cantilevered bottom portion 170 of calf shell 120 is drawn anteriorly so that collar 185 securely grips the anatomy of the patient in the region proximal (i.e., superior) to the calcaneus (FIG. 10). In essence, collar 185 "nestles" around the Achilles tendon, just above the calcaneus, thereby providing an enhanced gripping of the leg of the patient. As a result, when a distally-directed distraction force is thereafter applied to binding 35, the portions of binding 35 gripping the anatomy just proximal (i.e., superior) to the calcaneus are unable to slip past the calcaneus, due to the tight engagement of the binding on the anatomy just proximal (i.e., superior) to the calcaneus.

It should also be appreciated that since plantar shell 115 and calf shell 120 are separated by a gap, and since curved portion 145 of long, narrow spine 105 is spaced away from the heel of the patient, binding 35 is open in the region of the heel of the patient and does not cover the heel of the patient or otherwise engage the heel of the patient. As a result, as the foot and lower leg of the patient are gripped by anatomical gripping system 5, there is space for the more pronounced calcaneus bone to move posteriorly without engaging long, narrow spine 105.

Additionally, the use of rotary tightening mechanisms 275A, 275B and 275C helps to accommodate a variety of foot sizes. More particularly, because binding 35 tightens around the patient anatomy based on the tensioning of cables 270A, 270B and 270C, patient feet of various sizes can be accommodated. The construction of the present invention also allows for the amount of tension applied to each rotary tightening mechanism 275A, 275B and 275C to be adjusted as needed for each patient in order to provide a secure and comfortable fit around the foot and lower leg of a patient.

In essence, anatomical gripping system 5 is designed to securely grip the essential anatomy of the patient without requiring the adjacent non-essential anatomy to be tightly squeezed, thus reducing the pressure that the remaining surfaces of the foot receive. Gripping the foot using the prominent bones of the foot (i.e., the calcaneus and malleoli bones) ensures a secure grip of the foot while minimizing trauma to the foot anatomy. Among other things, by engaging the anatomy proximal (i.e., superior) to the malleoli and the calcaneus, subsequent pulling of the leg distally (e.g., for leg distraction) applies the pulling force along the axis of the leg, whereby to produce less trauma on the anatomy. This approach is in sharp contrast to the approach of conventional surgical boots, which seek to tighten down the surgical boot around the front of the foot, in a relatively focal zone which contains soft tissues, nerves and blood supply. This conventional approach can lead to injury if the surgical boot is excessively tightened, but can also lead to slippage if tightening of the surgical boot is not sufficient.

And significantly, even though no portion of binding 35 covers or engages the heel of the patient, a superior grip is achieved on the patient's anatomy, and problematic "heel slippage" is avoided.

It should also be appreciated that a key aspect of the present invention is the ability to conform plantar shell 115, calf shell 120 and anterior shell 125 to the shape of the patient's foot and lower leg. This is achieved by, among other things, (i) forming plantar shell 115 with flanges 155 and 156, with the flanges being separated by openings 157, (ii) forming calf shell 120 with flanges 175 and 180, with flanges 175 and 180 being separated by openings 187, and with bottom portion 170 of calf shell 120 cantilevered away from long, narrow spine 105, and (iii) forming anterior shell 125 with flanges 235, 245 and 255, with the flanges being separated by openings 300 and 305, respectively, and with openings 310, 315 and 320 being formed in anterior shell 125, whereby to provide significant flexibility for shells 115, 120 and 125, which both improves gripping performance and enables a single size of binding 35 to accommodate substantially all foot sizes.

Foot Sizing

In a preferred embodiment, a single size binding 35 is able to adequately grip the legs of patients of substantially all sizes. To help ensure an adequate grip is achieved for patients of substantially all sizes, soft liner 30 and/or soft butterfly wrap 25 can be provided in two or more sizes (e.g., small, medium and large). For smaller feet, soft liner 30 and/or soft butterfly wrap 25 may be supplemented with additional material, e.g., non-compressible or compressible foam, so as to provide the patient with the same "effective" foot size as a patient with a larger foot, allowing for a single size of binding 35 to be used. In one embodiment, this additional material is added to the bottom and/or back of soft liner 30 and/or soft butterfly wrap 25. In another embodiment, this additional material is added to the top and/or front of soft liner 30 and/or soft butterfly wrap 25.

By way of example but not limitation, in another form of the invention, and looking now at FIGS. 25-28, plantar shell 115 and calf shell 120 of binding 35 may comprise rigid foam portions 290 disposed on the interior surfaces of plantar shell 115 and calf shell 120. If desired, rigid foam portions 290 may be provided in a variety of thicknesses to accommodate different size feet and legs. In another embodiment, rigid foam portions 290 may be custom-formed to each patient's foot and leg prior to the surgical procedure. In any case, providing plantar shell 115 and/or calf shell 120 with rigid foam portions 290 enables the foot and lower leg of the patient to be received in binding 35 to optimize gripping of the foot and lower leg of the patient in the binding. By way of further example but not limitation, plantar shell 115 may comprise different thickness rigid foam portions 290 so as to compensate for different size feet, such that the calcaneus bone of the patient is consistently positioned within binding 35. For example, a smaller foot may require a thicker rigid foam portion 290 on plantar shell 115, whereas a larger foot may require a thinner rigid foam portion 290 on plantar shell 115.

In an alternative embodiment, a second size of binding 35 may be used to accommodate a smaller or larger foot size.

In this embodiment, soft liner 30 and/or soft butterfly wrap 25 may be provided in a single size. Alternatively, soft liner 30 and/or soft butterfly wrap 25 may be provided in a second size; in this embodiment, soft liner 30 and/or soft butterfly wrap 25 may comprise padding as described above (e.g., on the top and/or front, or on the back and/or bottom, of soft liner 30 and/or soft butterfly wrap 25). These scaled bindings are scaled with respect to the key anatomical features and the areas of load transfer established with the soft butterfly wrap 25 and soft liner 30. Scaling will not be proportional over the entire device, but will scale according to the key measures of the foot and leg anatomy (e.g., ankle diameter, malleoli heights, etc.).

Use of Anatomical Gripping System 5

In use, when a patient's leg is to be distracted, soft butterfly wrap 25 and soft liner 30 are positioned about the foot and lower leg of the patient so that lower band 40 of soft butterfly wrap 25 sits around the forefoot and midfoot of the patient, and upper band 45 of soft butterfly wrap 25 sits above (i.e., "proximal to" or "superior to") the malleoli of the patient, and soft liner 30 is positioned about the foot and lower leg of the patient so as to cover a portion of the foot and lower leg of the patient. Where soft butterfly wrap 25 and soft liner 30 are formed as separate components, first soft butterfly wrap 25 is applied to the foot and lower leg of the patient, and then soft liner 30 is applied to the foot and lower leg of the patient (and over soft butterfly wrap 25). Then binding 35 is mounted to distraction frame 15 using mount 135 on the bottom of binding 35 (i.e., using mount 135 on plantar portion 140 of long, narrow spine 105). Next, the leg of the patient is inserted into binding 35 so that the foot of the patient seats in plantar shell 115 and the calf of the patient seats in calf shell 120. Then anterior shell 125 is brought over the anterior portion of the foot and lower leg of the patient, and over the sides of plantar shell 115 and calf shell 120. Pull tabs 280A, 280B and 280C are then used to place cables 270A, 270B and 270C over plantar cable mounts 140, lower calf cable mounts 190 and upper calf cable mounts 195, respectively. Next, rotary tightening mechanisms 275A, 275B and 275C are tightened so as to cause binding 35 to grip the anatomy of the patient in the region of (i) lower band 40 of soft butterfly wrap 25, (ii) upper band 45 of soft butterfly wrap 25, and (iii) the lower to mid-calf of the patient. Note that as rotary tightening mechanism 275B is used to tighten cable 270B, anterior shell 125 moves posteriorly, and bottom portion 170 of calf shell 120 flexes anteriorly, whereby to provide a secure grip on the anatomy of the patient. Then distraction frame 15 is used to distract the hip joint of the patient by applying a distal force to mount 135 of binding 35 (and hence applying a distal force to the distal end of the leg of the patient).

At any point in the surgical procedure, tension can be released from binding 35 by any member of the surgical staff who is in the sterile field. This can be done without compromising sterility. More particularly, and looking now at FIGS. 29-31, a member of the surgical staff's grips rotary tightening mechanism 275A, 275B and/or 275C through a sterile drape 295 and pulls it upward to release the rotary tightening mechanism. In other words, the member of the surgical staff depresses the sterile drape over the sides of the rotary tightening mechanism(s), grips the side(s) of the rotary tightening mechanism(s) and pulls the rotary tightening mechanism(s) upward until it/they is/are released. This can be done without the risk of tearing the sterile drape because the rotary tightening mechanisms have a rounded shape without any sharp edges. Additionally, the motion to release the rotary tightening mechanisms is a short, vertical motion that does not put stress on the sterile drape.

In an alternative method of use, if preferred, the foot and lower leg of the patient can be secured to binding 35 before binding 35 is secured to distraction frame 15, and then binding 35 can be secured to distraction frame 15—in this case, a stand (not shown) may be provided for holding binding 35 steady while the foot and lower leg of the patient is secured to binding 35. In one form of this alternative method of use, the foot and lower leg of the patient are secured to binding 35 pre-operatively while the patient is still conscious and can provide feedback on the tightness of binding 35 (e.g., so as to ensure that binding 35 is tight but not too tight). In this alternative method of use, the patient may be conscious and provide feedback to the surgical staff on the comfort level of binding 35 as binding 35 is secured to their foot and lower leg. For example, if binding 35 is uncomfortably tight, the binding could be loosened or, if binding 35 feels too lose, binding 35 can be tightened. In this alternative form of the invention, and looking now at FIG. 32, long, narrow spine 105 of binding 35 may have a modified configuration to facilitate a patient walking while binding 35 is on their foot, e.g., long, narrow spine 105 may comprise an enlarged heel 400 and a rubber sole 405.

Additional Constructions

In another form of the invention, soft liner 30 may be incorporated into plantar shell 115, calf shell 120 and anterior shell 125 of binding 35. In this form of the invention, soft butterfly wrap 25 is formed as a separate component and is placed on the patient as a first step prior to the patient's foot being placed into binding 35 (which incorporates soft liner 30).

In some cases, it can be helpful to know the level of force being applied to the foot and lower leg of the patient by binding 35, and/or to limit the level of force being applied to the foot and lower leg of the patient by binding 35.

Figure 33:
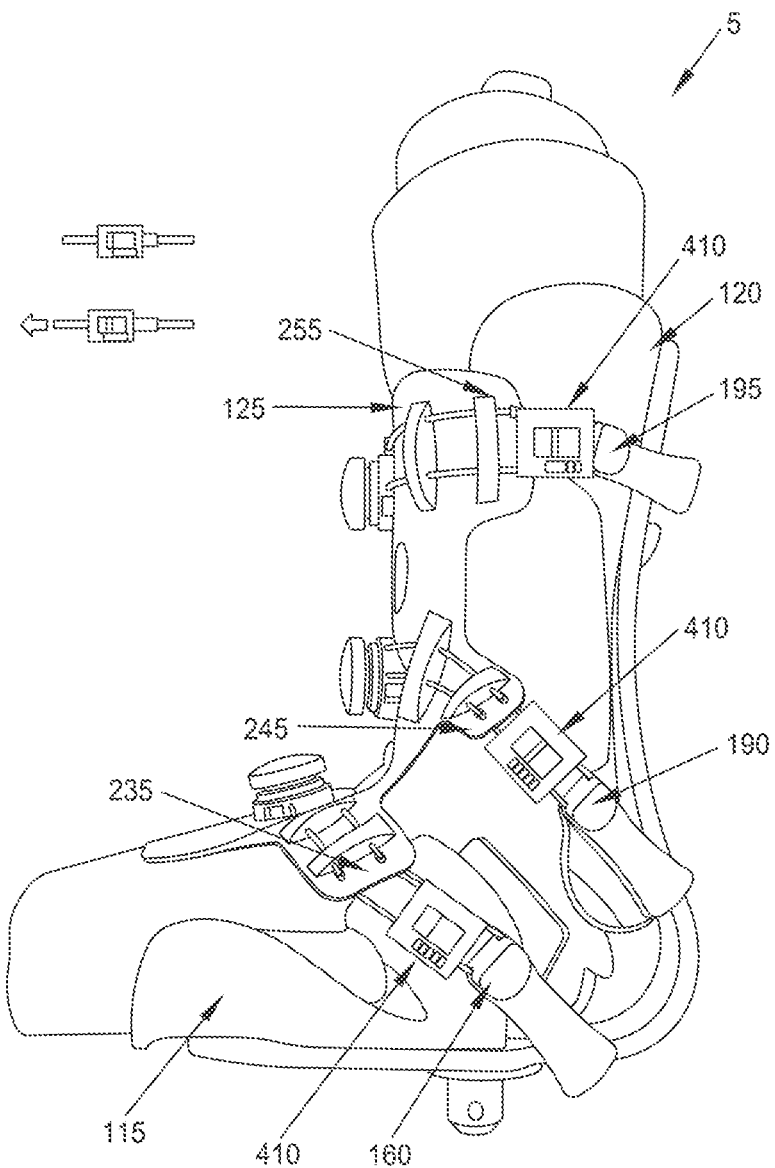

By way of example but not limitation, in one form of the invention, and looking now at FIG. 33, force gauges 410 are incorporated into binding 35 to measure the active tension being applied to cable assemblies 130A, 130B and 130C by rotary tightening mechanisms 275A, 275B and 275C. The provision of force gauges 410 is helpful inasmuch as it can provide the user with the ability to know how tight the binding is on the foot and lower leg of the patient.

In one construction, force gauges 410 may be constructed like a "fish scale" with a spring being located between two housing members. One housing member is connected to the portions of cable assemblies 130A, 130B or 130C leading to rotary tightening mechanisms 275A, 275B or 275C, and the other housing member is connected to the portions of cable assemblies 130A, 130B or 130C leading to cable mounts 160, 190 or 195. As tension is applied by rotary tightening mechanisms 275A, 275B and 275C, the tension in cable assemblies 130A, 130B and 130C will increase. As this occurs, the two housing members in force gauge 410 will move away from one another. An indicator on force gauge 410 provides a visual representation of the distance the two housing members will move away from one another, and hence a visual representation of the amount of tension in cable assemblies 130A, 130B and 130C.

In another form of the invention, force gauge 410 may be incorporated into plantar shell 115 and calf shell 120, e.g., into plantar cable mount 160 and into lower calf cable mount 190 and upper calf cable mount 195.

Figure 34:
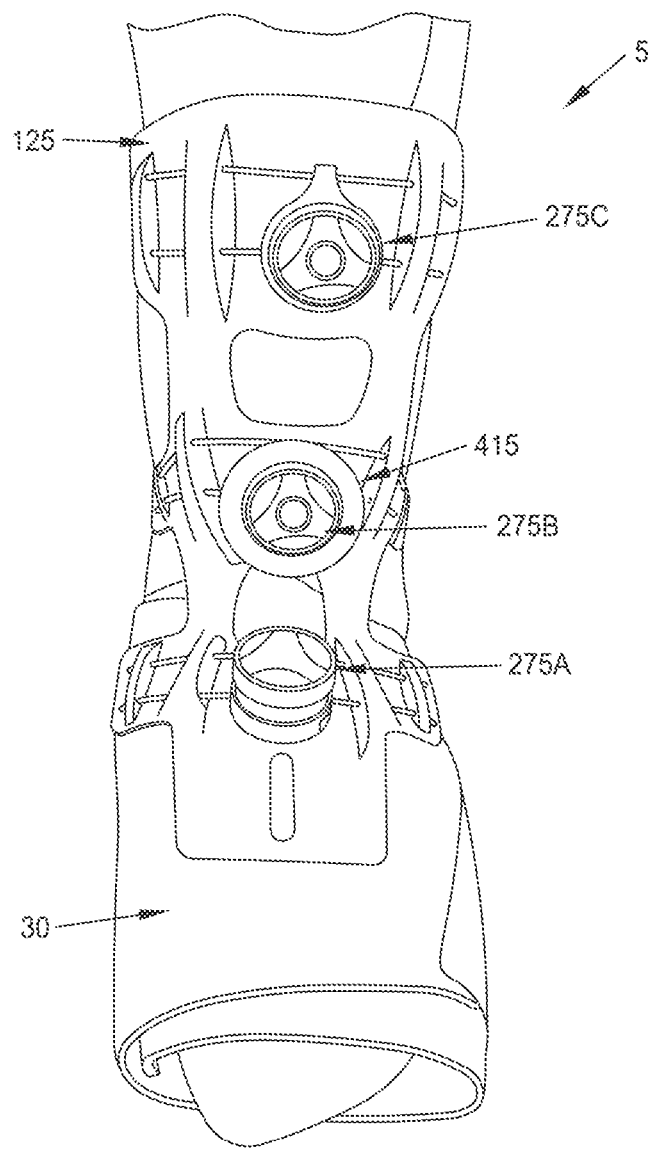

In another form of the invention, and looking now at FIG. 34, a torque limiter 415 is coupled to, or incorporated into, one or more of rotary tightening mechanisms 275A, 275B and 275C. In this form of the invention, torque limiter 415 will "slip" at a pre-determined torque threshold, i.e., torque limiter 415 will limit the maximum possible torque which can be applied by one or more of rotary tightening mechanisms 275A, 275B and 275C. This torque threshold may be adjustable by the user, or the torque threshold may be a fixed value set at the time of manufacture. In either case, as the torque applied to rotary tightening mechanisms 275A, 275B and 275C passes or exceeds the pre-determined torque threshold, torque limiter 415 will "slip" (as in a friction plate or slip-clutch), or uncouple the load entirely, thereby preventing additional torque from being applied to rotary tightening mechanisms 275A, 275B and 275C (and thus preventing additional torque from being applied to cable assemblies 130A, 130B and 130C).

Modifications of the Preferred Embodiments

It should be understood that many additional changes in the details, materials, steps and arrangements of parts, which have been herein described and illustrated in order to explain the nature of the present invention, may be made by those skilled in the art while still remaining within the principles and scope of the invention.

What is claimed is:

1. An anatomical gripping system for gripping a lower leg and foot of a patient, the anatomical gripping system comprising:
   a binding comprising:
   a rigid spine;
   a calf member directly mounted to the rigid spine and configured to extend along the calf side of the lower leg of the patient, the calf member comprising a first portion and a second portion, the second portion being movable relative to the first portion;
   a plantar member spaced from the calf member and configured to extend under the foot of the patient; and
   a tensioning mechanism configured to apply a force to the second portion of the calf member, whereby to hold the second portion of the calf member superior to the calcaneus bone of the patient.

2. The anatomical gripping system according to claim 1, wherein the tensioning mechanism is connected to the second portion of the calf member.

3. The anatomical gripping system according to claim 1, wherein the plantar member is mounted to the rigid spine.

4. The anatomical gripping system according to claim 1, wherein the tensioning mechanism comprises a force gauge for measuring the force applied by the tensioning mechanism.

5. The anatomical gripping system according to claim 1, wherein the first portion of the calf member is mounted to the rigid spine.

6. The anatomical gripping system according to claim 1, wherein the second portion comprises a cantilever.

7. The anatomical gripping system according to claim 1, wherein the binding further comprises an anterior member.

8. The anatomical gripping system according to claim 7, wherein the tensioning mechanism is connected to the anterior member.

9. The anatomical gripping system according to claim 1, wherein the force applied by the tensioning mechanism comprises an anteriorly-directed force.

10. The anatomical gripping system according to claim 1, wherein the second portion of the calf member is drawn into the superior portion of the calcaneus bone when the tensioning mechanism applies the force to the second portion of the calf member.

11. The anatomical gripping system according to claim 1, wherein when a traction force is applied to the leg of the patient, the second portion of the calf member is configured to inhibit relative motion between the calcaneus bone of the patient and the binding.

12. The anatomical gripping system according to claim 10, wherein when a traction force is applied to the leg of the patient, the second portion of the calf member is configured to inhibit relative motion between the calcaneus bone of the patient and the binding.

13. The anatomical gripping system according to claim 7, wherein the tensioning mechanism is configured to apply a tensioning force between the anterior member and the calf member, whereby to grip the lower leg of the patient above the malleoli bones.

14. The anatomical gripping system according to claim 1, wherein the binding further comprises a soft wrap for covering at least a portion of the lower leg.

15. The anatomical gripping system according to claim 14, wherein the soft wrap is configured to cover the lower leg of the patient superior to the malleoli bones.

16. The anatomical gripping system according to claim 14, wherein the tensioning mechanism is configured to apply a tensioning force onto the soft wrap.

17. The anatomical gripping system according to claim 1, wherein the binding further comprises a second tensioning mechanism which is connected to the plantar member.

18. The anatomical gripping system according to claim 1, wherein the binding further comprises a second tensioning mechanism, wherein the second tensioning mechanism is configured to be connected to the calf member adjacent to the calf of the lower leg of the patient.

19. An anatomical gripping system for gripping a lower leg and foot of a patient, the anatomical gripping system comprising:
   a binding comprising:
   a rigid spine extending from the lower leg to the foot of the patient;
   a calf member configured to extend along the calf of the lower leg of the patient, the calf member comprising a first portion and a second portion, wherein the first portion of the calf member is directly mounted to the rigid spine, wherein the second portion of the calf member extends inferiorly from, and is flexible relative to the first portion;
   a plantar member spaced from the calf member and configured to extend under the foot of the patient; and
   a tensioning mechanism configured to apply a force to the second portion of the calf member, whereby to hold the second portion of the calf member superior to the calcaneus bone of the patient.

20. The anatomical gripping system according to claim 19, wherein the binding further comprises an anterior member.

21. The anatomical gripping system according to claim 19, wherein the tensioning mechanism is configured to apply a tensioning force between the anterior member and the calf member, whereby to grip the lower leg of the patient above the malleoli bones.

22. The anatomical gripping system according to claim 19, wherein the binding further comprises a second tensioning mechanism which is connected to the plantar member.

23. The anatomical gripping system according to claim 19, wherein the binding further comprises a second tensioning mechanism, wherein the second tensioning mechanism is configured to be connected to the calf member adjacent to the calf of the lower leg of the patient.

24. The anatomical gripping system according to claim 19, wherein the binding further comprises a soft wrap for covering at least a portion of the lower leg.

25. The anatomical gripping system according to claim 24, wherein the soft wrap is configured to cover the lower leg of the patient superior to the malleoli bones.

26. The anatomical gripping system according to claim 24, wherein the tensioning mechanism is configured to apply a tensioning force onto the soft wrap.

27. The anatomical gripping system according to claim 19, wherein when a traction force is applied to the leg of the patient, the second portion of the calf member is configured to inhibit relative motion between the calcaneus bone of the patient and the binding.

28. The anatomical gripping system according to claim 19, wherein the tensioning mechanism is connected to the second portion of the calf member.

29. The anatomical gripping system according to claim 19, wherein the plantar member is mounted to the rigid spine.

30. The anatomical gripping system according to claim 19, wherein the tensioning mechanism comprises a force gauge for measuring the force applied by the tensioning mechanism.

31. The anatomical gripping system according to claim 19, wherein the second portion comprises a cantilever.

32. The anatomical gripping system according to claim 20, wherein the tensioning mechanism is connected to the anterior member.

33. The anatomical gripping system according to claim 19, wherein the force applied by the tensioning mechanism comprises an anteriorly-directed force.

* * * * *